United States Patent [19]

Cox et al.

[11] Patent Number: 5,589,211

[45] Date of Patent: *Dec. 31, 1996

[54] METHODS FOR PROCESSING POULTRY SHELL EGGS

[76] Inventors: James P. Cox; R. W. Duffy Cox; Jeanne M. Cox, all of 246 E. Bartlett Rd., Lynden, Wash. 98264

[ * ] Notice: The portion of the term of this patent subsequent to Aug. 19, 2011, has been disclaimed.

[21] Appl. No.: 156,273

[22] Filed: Nov. 22, 1993

Related U.S. Application Data

[63] Continuation-in-part of Ser. No. 746,940, Aug. 19, 1991, which is a continuation-in-part of Ser. No. 674,495, Mar. 25, 1991, Pat. No. 5,283,072, which is a continuation of Ser. No. 349,974, May 8, 1989, abandoned, which is a continuation of Ser. No. 196,878, May 19, 1988, abandoned, which is a continuation of Ser. No. 70,597, Jul. 8, 1987, abandoned, which is a continuation of Ser. No. 758,086, Jul. 23, 1985, abandoned.

[51] Int. Cl.[6] .................................................. A23B 5/005
[52] U.S. Cl. ........................ 426/298; 426/300; 426/614; 426/521
[58] Field of Search .................................. 426/614, 298, 426/300, 521

[56] References Cited

U.S. PATENT DOCUMENTS

| | | |
|---|---|---|
| 1,163,873 | 12/1915 | Thornburgh . |
| 1,888,415 | 11/1932 | Swenson . |
| 1,922,143 | 8/1933 | Sharp . |
| 2,001,628 | 5/1935 | Nierinck . |
| 2,184,063 | 12/1939 | Meyer et al. . |
| 2,236,773 | 4/1941 | Fischer . |
| 2,423,233 | 7/1947 | Funk . |
| 2,497,817 | 2/1950 | Hale et al. ............................. 426/300 |
| 2,673,160 | 5/1954 | Feeney et al. . |
| 2,758,935 | 8/1956 | Shaffer . |
| 2,776,214 | 1/1957 | Lloyd et al. . |
| 3,028,245 | 4/1962 | Mink et al. . |
| 3,082,097 | 3/1963 | Haller . |
| 3,144,342 | 8/1964 | Collier et al. . |
| 3,148,649 | 9/1964 | Moore et al. . |
| 3,364,037 | 1/1968 | Mink et al. . |
| 3,522,061 | 7/1970 | Whiteford . |
| 3,658,558 | 4/1972 | Rogers et al. . |
| 4,524,082 | 6/1985 | Liot ......................................... 426/312 |
| 4,524,083 | 6/1985 | Liot ....................................... 426/330.1 |
| 4,808,425 | 2/1989 | Swartzel et al. ........................ 426/399 |
| 4,957,759 | 9/1990 | Swartzel et al. ........................ 426/399 |

FOREIGN PATENT DOCUMENTS

| | | | |
|---|---|---|---|
| 72454 | 4/1953 | Netherlands ................................ 53/5 |

OTHER PUBLICATIONS

Carter et al. 1986. The New Good House–Keeping Cookbook. pp. 288–289.
E. M. Funk, Maintenance of Quality in Shell Eggs By Thermostabilization, Research Bulletin 467, University of Missouri, College of Agriculture, Agriculture Experiment Station, Dec. 1950.
E. M. Funk, Pasteurization of Shell Eggs, Research Bulletin 364, University of Missouri, College of Agriculture, Agricultural Experiment Station, May 1943.
E. M. Funk, Stabilizing Quality in Shell Eggs, Research Bulletin No. 362, University of Missouri, College of Agriculture, Agriculture Experiment Station, Apr. 1943.
Murphy and Sutton, Pasteurization of Shell Eggs to Prevent Storage Rot and Maintain Quality, A Progress Report of Experimental Work, Publication No. 3317, Department of Agriculture, New South Wales, Austrailia, 1947.

Primary Examiner—Anthony J. Weier
Attorney, Agent, or Firm—Hughes, Multer & Schacht

[57] ABSTRACT

Time at temperature methods of treating whole eggs which make them safer to eat without affecting the functionality or organoleptic properties of the eggs. The keeping quality of the eggs is also improved.

3 Claims, 12 Drawing Sheets

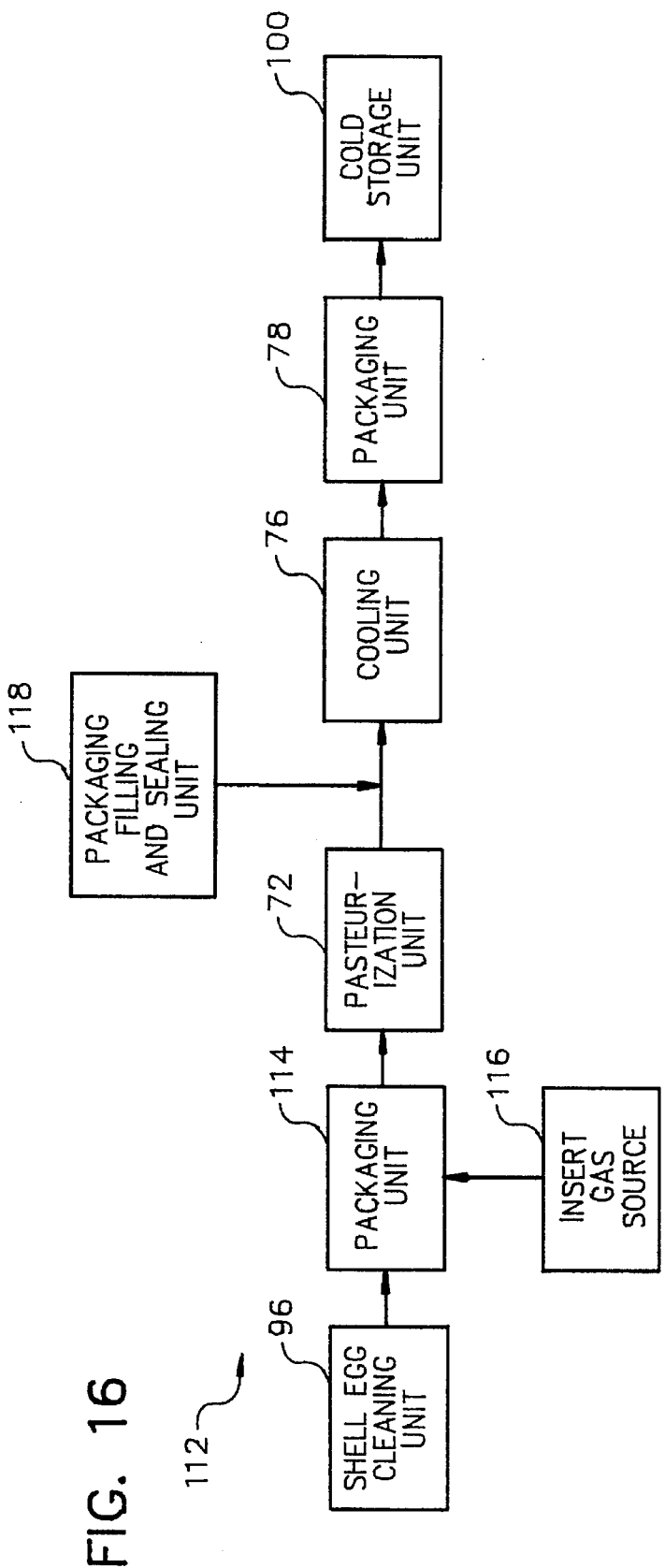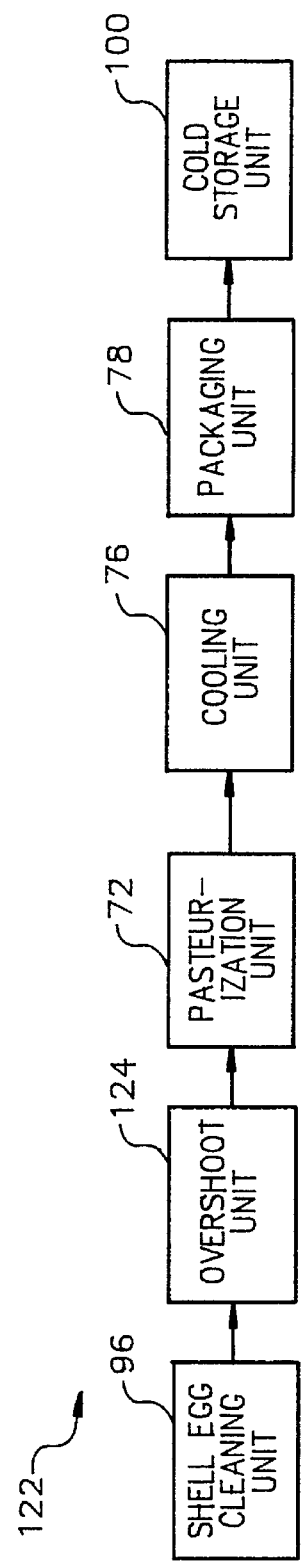

METHODS FOR PROCESSING POULTRY SHELL EGGS

CROSS REFERENCES TO RELATED APPLICATIONS

This application is a continuation-in-part of U.S. application Ser. No. 07/746,940 filed Aug. 19, 1991. The parent application is a continuation-in-part of U.S. application Ser. No. 07/674,495 filed Mar. 25, 1991, now U.S. Pat. No. 5,283,076 which was a continuation of U.S. application Ser. No. 07/349,974 filed May 8, 1989, and abandoned, which was a continuation of U.S. application Ser. No. 07/196,878 filed May 19, 1988, and abandoned, which was a continuation of U.S. application Ser. No. 07/070,597 filed Jul. 8, 1987, and abandoned, which was a continuation of U.S. application Ser. No. 06/758,086 filed Jun. 24, 1985, and abandoned.

TECHNICAL FIELD OF THE OF THE INVENTION

The present invention relates to poultry shell eggs of overall improved food safety quality and to shell egg pasteurization methods with time and temperature process parameters equivalent to or exceeding those minimum standards established by the United States Department of Agriculture (USDA) for whole liquid eggs.

DEFINITIONS

Functionality or Functional Properties: Eggs contribute to the volume, structure, texture, and keeping quality of baked products. The coagulation of egg proteins during heating brings about the thickening of custards and pie fillings and the binding of pieces of food together as in loaves or croquettes. When eggs are whipped, the proteins form elastic films and incorporate air that provides the leavening and volume needed in such products as angel food cakes, souffles, sponge cakes, and meringues. The foam structure of these products is made rigid by coagulation of the protein during baking. The elasticity of egg protein films is also important in popovers and cream puffs; the protein films stretch when steam is produced during baking and later coagulate to form the framework of the product. Lipoproteins of the yolk are good emulsifying agents. They make it possible to disperse the oil in the other ingredients and thereby contribute to the consistency of mayonnaise and salad dressings and the structure of cream puff shells.

Whole eggs are used in sponge and layer cakes, bread, and rolls. Yolks are used in mayonnaise and salad dressing, sweet goods, doughnuts, and cakes in which more yellow color is desired. Whites are used in angel food cakes, meringue toppings, puff pastry, white pound cakes, layer cakes, cupcakes, certain candies, and a number of premixed products.

The extent to which the functional properties are affected by pasteurization is determined by testing the performance of the eggs under conditions in which damage is readily observed.

Pasteurization (or Pasteurization Process) Temperature: The temperature at which a pasteurization medium (air or other gas, water, oil, or other fluid, etc.) is maintained for an RPT such that a destruction of any infections present in an egg at least equal to that obtained by observing the minimum or protracted standards mandated by the USDA for liquid whole eggs is obtained on the shell of the egg and throughout and in the furtherest reaches of the egg interior including the egg yolk. Pasteurization temperatures range from 130° F. to a temperature approaching but less than 140° F. (<140° F.).

EqT: The point at which all particles throughout the mass of a shell egg reach equilibrium with the selected pasteurization medium temperature and the point at which RPT begins. EqT time is the time required to obtain EqT of an egg.

Real Process Time (RPT): That part of the TPT after all particles throughout the mass of a shell egg have reached a selected pasteurization temperature enabling the meeting of the U.S. Department of Agriculture standards for liquid whole eggs.

Total Process Time (TPT): That total length of time for which an egg is heated beginning with the egg at an initial preprocessing temperature and ending when the application of heat to the egg is terminated. TPT equals EqT time plus RPT.

Throughout the mass of an egg: encompasses all matter in the shell of an egg and within the shell.

Temperatures are often expressed hereinafter in the form xxx to yyy° F. (±z° F.). This is to be interpreted as a temperature range in which the lower limit is a nominal xxx° F. with a tolerance of ±z° F. and the upper limit is a nominal yyy° F. with a tolerance of ±z° F.

BACKGROUND OF THE INVENTION

For many years minimum food safety processing standards for various commodities have been promulgated and enforced by the United State Department of Agriculture. While long enforced for liquid whole eggs and egg products of a wide variety, based upon minimum standards of pasteurization processing, food safety standards have never been established for shell eggs. Indeed, as a review of the prior art identified in this specification has shown, there has not heretofore even been available technology for successfully pasteurizing shell eggs to acceptable standards, that is, to standards equaling USDA guidelines established for the other egg products mentioned above.

Shell eggs are an important commodity affording the consumer many nutritional advantages unparalleled by any other food product. These advantages include very favorable costs per nutritional unit of food value, convenience of preparation, gastronomic enjoyability, culinary usefulness, and availability.

It has long been known that some shell eggs contain infectious organisms such as *Salmonella* which, from a food safety standpoint, is of primary concern. Techniques for improving the food safety of shell eggs by destroying these infectious microorganisms have been proposed. However, aside from those effective for external sanitation, none are known to have ever been successfully employed. Instead, processing, handling, and other aspects of egg production have been emphasized in an effort to indirectly reduce the magnitude of the problem.

Awareness and concerns regarding infectious organisms in the yolk of a shell egg have been slow in developing. Both awareness and concerns have been amplified increasingly over the past decade as a result of numerous outbreaks of food poisoning irrefutably attributable to such yolk-associated organisms.

Advanced social programs and medical care have made a vastly enlarged percentage of the population dramatically more vulnerable to toxic effects of such food borne infections. At increased peril are those significant segments of the population of increased longevity or those who are immunocompromised due to organ transplants, immunosuppression therapies, and diseases caused by or causing compromised immune systems such as AIDS.

Increasingly, concerns over the safety of eggs consumed as a food illuminate the issue of transovarian infection developed deep inside the egg as it is formed in the oviduct. In addition, infectious organisms are known to penetrate the pores of shells and perhaps even the vitelline membranes of eggs, contaminating deeper proteins including the yolks. Also, for reasons not entirely clear, diseased hens are now known to excrete microorganisms inside the egg. The offending microorganism currently identified with this problem is *Salmonella enteritis* (*S. enteritis*).

*Salmonella* are small, gram negative, nonsporing rods. They are indistinguishable from *Escherichia coli* (*E. coli*) under the microscope or on ordinary nutrient media. All species and strains are currently presumed to be pathogenic for man.

As a disease organism, *Salmonella* produces a variety of illnesses depending on the species. *S. typhimurium,* which translates to "*Salmonella* from Typhus Mary", needs no other explanation. *S. typhi* causes enteric fever. *S. paratyphi* type A and type B cause a syndrome which is similar to but milder than typhus.

Reported cases of severe gastroenteritis (stomach flu) have implicated *S. bareilly, S. newport,* and *S. pullorum* as well. The mortality range is primarily based on the victim's age and general health. *S. choleraesuis* has the highest reported mortality rate at 21%.

*S. senftenberg* is reputedly the most heat resistant specie of *Salmonella*. It is reportedly destroyed at 130° F. (54.4° C.) after 2.5 minutes. It is estimated that *S. senftenberg* 775W is 30 times more heat resistant than *S. typhimurium*. Turkeys (10 to 11 lbs.) inoculated with 115,000,000 microorganisms of *S. pullorum* required holding at an average internal temperature of 160° F. (71.1° C.) for four hours and 55 minutes before the bacteria were destroyed.

Over 2,000 other species of *Salmonella* are known. The number increases yearly.

Among the most common vehicles for food poisoning caused by Salmonella are eggs. Widespread publicity on illnesses and deaths attributed to contaminated eggs containing *S. enteritis* in Europe over the past few years has reportedly resulted in a reduction in egg consumption. In some distinct marketing areas the reduction has been estimated to be as great as 50 percent. The problem is being perceived in Europe and in the United States as chronic, spreading, and a major public health challenge. Nevertheless, in the United States alone, approximately 240,000,000 dozen eggs are still consumed annually.

A recent article in the Nutrition Action Health Letter published by the Center for Science in the Public Interest (July/August 1991 edition, Volume 18, number 6, "NAME YOUR (FOOD) POISON") relates a current trend of growing concern. The article reports that, according to government estimates, 80,000,000 cases of food poisoning yearly result in about 9,000 deaths and several billions of dollars in health costs.

The article claims that the primary causative foods are, in order: dairy products, eggs, poultry, red meat, and seafood.

The article reports that 1 in 10,000 eggs is contaminated with *Salmonella enteritis*. The average American consumes about 200 eggs per year. If your egg consumption is average, your chance of downing an egg contaminated with one or more species of *Salmonella* is 1 in 50; or, put another way, it is likely that you will eat four contaminated eggs this year.

If you are over 65 or have a disease such as cancer or AIDS associated with a weakened immune system, the article advises: don't eat raw eggs; don't drink egg nog; don't eat Caesar salads, home made mayonnaise, ice cream, or "health" drinks that call for raw eggs. Cook all eggs thoroughly—solid white and yolk.

Compounding the contamination problem is the improper handling of eggs in institutional and even home settings. Often cited is the all too frequent observation of eggs setting out at room temperature for long periods of time in institutional kitchens. Such unknowledgeable treatment promotes bacterial advancement in even the freshest egg.

Little is known about virology inside the egg. It has long been and is still believed by some that shell eggs are sterile inside the shell. Needle puncture samples of the inside of an egg including both yolk and white taken under aseptic conditions usually do demonstrate a negative plate count when cultured. Nevertheless, it is well known that, when eggs are broken in quantity, they immediately demonstrate significant gross populations of infectious microorganisms. It is not unusual to find plate counts ranging from several hundred to many thousands, even when the surface of the egg shells have been cleaned of filth and washed in the best antiseptics known to food science. The occurrence of *S. enteritis* inside the shell egg is now also well documented.

One source of infection arises from the fact that egg shells have numerous pores which permit the egg to breathe. Pore holes vary in size. When the egg is laid, those holes come into contact with organic refuse in the cage. It is very likely that some microbes contacting the egg are of a size which allows them to fit through the pores. Once inside, the microbes are not uniformly spread around the interior of the egg but are retained in small patches on the inner shell membrane, which has yet smaller pores than the shell.

Washing actually spreads microbes more evenly, increasing contamination through greater surface contact with entry pores in the egg shell. When the eggs are cracked, the shell membranes may be ripped and torn loose. And, when the shells are subsequently emptied, the eggs may be peppered with this stored inoculum in addition to airborne bacteria.

Also, as egg temperatures vary, there is active and ongoing gas and vapor exchange between the yolk and white via the vitelline membrane, between the white and the inside of the shell via the outer and inner shell membranes, and also between the shell and the outside environment. Airborne microorganisms can also reach the interior of the egg through these mechanisms.

Finally, as discussed above, eggs can be, and frequently are, contaminated by transovarian infection. The extent of this problem is still not known. Thus, an egg may be unsafe to eat even if there is no transport of harmful microorganisms from the exterior of the egg to its interior. Worse yet is when both of the egg infecting mechanisms—pore penetration and transovarian infection—are at work.

U.S. Pat. No. 4,808,425 issued Feb. 28, 1989 to Swartzel et al. elaborates on the USDA standards for pasteurizing liquid eggs, summarizes the disclosures of many references, identifies resources relative to egg pasteurization, and adequately points out many of the problems associated with available techniques for making liquid but not shell eggs of safer food quality. Swartzel et al. employ a conventional pasteurization technique—time at temperature—to treat liquid egg products. The products are contacted against a heated surface at high temperatures; i.e., above 140° F. (60° C.) for short durations of less than 10 minutes. This approach is not applicable to a shell egg.

The minimum time at temperature processing mandated by USDA standards produces liquid eggs which are safe to eat because all particles have been exposed to RPT; and, if the liquid eggs are carefully processed, an at least acceptable degree of functionality and other valued properties can be retained. Standards for shell eggs are lacking because, up to now, a reliable time at temperature technique for making shell eggs safe to eat has not existed. In particular, there is not known to exist any effective process which can be employed to process whole eggs to the standards mandated for liquid eggs; i.e., to ensure that all particles throughout the mass of the egg—which includes the shell, the outer shell and egg membranes, the albumen layers or egg white, the chalaza, the vitelline membrane, and the yolk to its innermost reaches or center—are exposed to appropriate temperatures for times adequate for an acceptable kill of any harmful organisms that might be present.

Other researchers have focused their attention on time and temperature treatments for devitalization of vital shell eggs. To a much lesser extent, pasteurization of shell eggs to improve food safety quality has been considered.

Funk (Stabilizing Quality in Shell Eggs, Missouri Agricultural Experimental Station, Research Bulletin no. 362 and Maintenance of Quality in Shell Eggs by Thermostabilization, Missouri Agricultural Experimental Station, Bulletin no. 467) and Murphy and Sutton (Pasteurization of Shell Eggs to Prevent Storage Rot and Maintain Quality—a Progress Report of Experimental Work, Misc. Publication no. 3317, Department of Agriculture, New South Wales, Australia) purported to preserve shell eggs by briefly heating the eggs for 15 or 16 minutes at temperatures ranging from 130° to 135.9° F. (54.4° C. to 57.7° C.) and from 129.2° to 136.4° F. (54° C. to 58° C.). Irrespective of the starting temperature of the shell egg to be processed, these prior art processes cannot possibly provide a *Salmonella* free or *Salmonella* reduced inner egg. Neither can they achieve equivalents of the minimum requirements established by the USDA for processing liquid whole eggs.

The growth of external food poisoning infections are in some of the TPT/temperature ranges provided favorably influenced in the outermost layers of the shell egg. In many other ranges, external food poisoning infections will be significantly worsened. In all cases, temperatures near and at the egg yolk center never achieve the minimum temperature needed for a time effective to kill significant concentrations of infectious microorganisms.

On the contrary, because the internal temperatures reached near or in the center of the yolk are not high enough to destroy *Salmonella* and other infectious microorganisms, these prior art techniques, irrespective of how employed or combined, cannot meet accepted minimum standards for other egg products and by and large can only attain temperatures in the yolk within the times suggested which are in a range that will cause substantial increases of any food poisoning infections present therein. Within a very narrow range of those parameters, processed eggs may or may not become more infected. In all other instances a shell egg carrying a minor, non-lethal infection in the yolk can by use of such methods deteriorate markedly and become a very significant health risk, if not a toxic food.

In his U.S. Pat. No. 2,423,23 issued Jul. 1, 1947, Funk is concerned principally with "sterilizing or devitalizing" embryos in vital shell eggs. Confusingly, Funk ambiguously and interchangeably uses the term sterilization, stabilization, devitalization, and pasteurization in describing this objective. Funk claims that poultry eggs can be pasteurized, stabilized, and devitalized of embryonic life by immersing freshly laid, room temperature eggs in oil or water at temperatures ranging from 110° F. to 145° F. (43.3° C. to 62.8° C.) for times ranging from five to forty minutes or presumably, in the alternative, from 110° F. to 145° F. for from forty to five minutes.

Funk did not account for the fact that infectious microorganisms such as *Salmonella* are to be found throughout and in any or all specific parts of an egg, such as the yolk, whites, and membranes and even at the center of the yolk. Funk is principally concerned with devitiating the shell egg embryo and only with "destroying bacteriological organisms which may have penetrated the egg shell and . . . extended even so far as the yolk . . . ." He did not disclose in his patent or take into account the fact that the time required for processing a shell egg to make it safe to eat at specified temperatures is one thing for the outer, non-yolk portion of a shell egg and quite another for the center of the yolk. The result is that most of the process conditions claimed by Funk only result in conditions which at best can not meaningfully improve any preexisting infectious condition and at worst are certain to significantly increase health hazards from food poisoning infections. As applied to a shell egg, Funk cannot achieve even the minimum USDA processing standards (see FIG. 2) for liquid egg products. Use of other time/temperature combinations embraced by the broad statements in the Funk patent (which also cannot meet the minimum processing standards referred to above) result in the whites of the eggs being visibly cooked (see FIG. 8).

The Funk process parameters are temperature and TPT. As defined above, this is the total time a shell egg is held in a pasteurization medium heated to a selected pasteurization process temperature. This is quite different from the critical RPT, which is that portion of TPT in which all particles throughout the mass of the egg including those at the center of the yolk are at an effective pasteurization temperature measured from the point at which EqT is reached. There is no evidence that Funk recognized or appreciated the criticality of the difference between TPT and RPT. Even if he had, he presumably would not have made this distinction because, for purposes of devitiating an egg embryo, TPT and RPT are one and the same; i.e., there is little or no difference between these two process temperature conditions in pasteurizing, devitalizing, and sterilizing whole eggs to retard spoilage by making viable eggs infertile; i.e., by preventing ongoing embryonic development.

Lethal thermal damage to any part of an embryo, even only at its surface, is adequate for this purpose. Unlike the embryos in vital eggs, infections are composed of a multitude of micro-entities. Lethal damage at some point to a portion of this multifarious milieu is not adequate to destroy the infection as is the case with an embryo which may be killed if even a small part is heated to a high enough temperature. To be effective against infections frequently scattered throughout a substrate, the time at temperature must be adequate to kill large numbers of infectious organisms at these widely scattered locations. In a shell egg, that means that the pasteurization temperature must be reached and maintained for the necessary time throughout all parts of the egg containing the microorganisms. In this case, TPT and RPT are distinct; the distinction becomes increasingly critical as that mass of the egg which is potentially infectable is increased.

Funk's statement of process parameters for the devitalization of an egg embraces many time and temperature combinations which may be effective to achieve that object. However, when employed to kill food borne infections, those time and temperature combinations which apply to embryonic devitiation cannot adequately kill *Salmonella* or other harmful bacteria commonly found in eggs for reasons just discussed. The unfortunate fact is that most of those time/temperature combinations embraced in Funk can only significantly increase contamination inside the egg because they for the most part result in the egg being under conditions near to or optimal for maximum bacterial growth. An example is Funk's own preferred pasteurization parameters—five to ten minutes TPT at 138° F. (58.8° C.) and twenty to forty minutes TPT at 130° F. (54.4° C.).

Funk's preferred "pasteurization" method for a shell egg never achieves any RPT at the yolk but does achieve active growth range conditions there over a significant period of time. If the initial temperature of the shell egg is significantly lower than 70° F., as is or should always be the case in real world processing, Funk's preferred conditions will more seriously fail, resulting in dramatically favored conditions likely to increase any food poisoning infection present in the yolk.

Funk's preferred "pasteurization" process times and temperatures are not the worst cases suggested to one of ordinary skill in the art by his patent. Indeed, when many, if not most, of the Funk times and temperatures provided for pasteurization, sterilization, and devitalization of vital egg embryos are applied to the "pasteurization" of shell eggs to improve food safety quality, the results as confirmed by tests always fall short of and are often contrary to that objective. Moreover, as measured at the yolk, eggs processed pursuant to the most favorable possible conditions specified by Funk cannot meet the process standards provided in the USDA Protracted Whole Egg Standard for Liquid Whole Eggs (see FIG. 1) or even the minimum standards mandated by the USDA for liquid whole eggs (see FIG. 2).

For example, take a shell egg infected superficially at the inner shell surface (not uncommon) and also in the yolk (estimated to occur in 1 out of every 10,000 eggs). Pasteurize that egg according to Funk's specifications: from 40 minutes at 110° F. to 5 minutes at 140° F. At the lower temperature/longer time—40 minutes at 110° F.—the superficial temperatures even at the inner surface of the shell can be expected to promote the growth of bacteria and result in substantial worsening of any food poisoning infections present. Those temperatures achieved near or at the yolk center could reach but would never exceed the optimal growth conditions for food poisoning infections of *Salmonella*. The result, if infections were present, could easily be catastrophic increases in food poisoning concentrations. At shorter times and higher temperatures such as 134°–136° F., the temperature of an infected yolk center would never exceed about 125° F., yielding only eggs with increased food poisoning potential.

If the above-discussed time/temperature relationships are reversed—5 minutes at 110° F. to 40 minutes at 140° F.—as is equally reasonable from Funk's claim 1 and other statements in his patent, the low temperature/short time relationships constitute what could reasonably be selected as optimal by a bacteriologist to best culture Salmonella in eggs as a growth medium. At the other end of the spectrum—the extreme high temperature/long time combination of 140° F. for 40 minutes—, the "pasteurized" eggs would be "hard-boiled" in at least the exterior layers. All inbetween permutations of Funk conditions are ineffectual at best to meet even the minimum processing conditions required by the USDA for liquid whole eggs as shown in FIG. 2.

At the same time, even starting with shell eggs already at 70° F., let alone at more realistic, lower, cold storage temperatures, shell eggs processed according to Funk in the near extreme regime (>139° F./39.2 to 40 minutes TPT) will never achieve the RPT near or at the egg center needed to meet the basic protracted USDA temperature/time regimes for liquid whole eggs. To make matters worse, when shell eggs are immediately immersed into liquid at extreme temperature differentials (greater than about 65° F.–70° F.) as they could well be in following Funk's teachings, a significant number will crack. Cracked eggs are a loss. They are difficult to handle, unmarketable to consumers and other purchasers of whole eggs, and exceptionally susceptible to contamination.

In short, by even the most generous interpretation, no obvious combination of Funk's sterilization, devitalization, or pasteurization temperatures and times (from 110° F. to 140° F. for 5 to 40 minutes or from 110° F. to 140° F. for 40 to 5 minutes) can achieve even the minimum, FIG. 2 USDA process standard for liquid whole eggs without "cooking" at least the egg whites to some extent; and this is unacceptable because of consumer rejection and resulting loss of functionality. It is more likely, because it is true in the large majority of the available time/temperature combinations, that the Funk process would, if the egg being processed is infected at the yolk and/or superficially on the shell's inner surface, increase rather than decrease, perhaps dramatically, any food poisoning hazard present. The process would surely promote the growth of or at best substantially leave unaffected any harmful microorganisms present in the egg.

Application of the Funk process to eggs almost certainly results in eggs dependably rid of a living embryo. But with respect to pasteurization designed to improve food safety of shell eggs and with the questionable exception of a few time and temperature combinations effective to reduce superficial inner shell infections, Funk's process is only likely to produce infected shell eggs which remain or are made more hazardous to consumers and/or which are visibly partially cooked at the outer layers.

New serotypes of infectious organisms continue to develop. Increased production, mass handling, and widespread distribution of food products continue to increase the risks of food poisoning. Food poisoning incidents related to eggs are not uncommon and may even be increasing. Almost all food products have well developed standards of processing for ensuring food safety. With respect to eggs and egg products, only shell eggs have no standards for pasteurization. The primary reason for this lack of food safety pasteurization standards as required for all other egg products is undoubtedly attributable to the lack of knowledge of an efficacious process for making shell eggs safer to eat. In practice, known processes such as the one discussed above and proposed by Funk are inefficacious and either fail completely to achieve any meaningful benefits or are highly likely if not certain to result in products with substantially increased health hazards from food poisoning.

SUMMARY OF THE INVENTION

Now discovered and disclosed herein are novel, practical methods for temperature and time pasteurization of a shell egg throughout its entire mass with a degree of effectiveness equaling or even exceeding that obtained by employing the USDA minimum and protracted standards for liquid whole eggs, thereby reducing to an acceptable level the possibility that the subsequent ingestion of the processed egg might cause food poisoning, typically an illness consisting of gastroenteritis and fever lasting for several days but a deadly threat if a person in one of the susceptible categories identified above is infected. At the same time, these novel shell egg pasteurization techniques do not unduly compromise the integrity, functionality, or quality of the egg.

Process temperatures capable of producing this significant advantage for commercial size eggs (54 to 68 grams) with an initial, pre-pasteurization temperature of 45° F. or higher are those in the range of from about 130° F. to near, but less than, 140° F. Temperatures substantially above 139° F. are not useful because: (1) the egg will in too many instances crack upon being subjected to pasteurization, and/or (2) whites will begin to visibly cook before the egg yolk pasteurization temperature at the center of the egg yolk has been achieved, let alone maintained long enough to meet pasteurization standards equivalent to those mandated by the USDA for liquid eggs. At temperatures below the specified minimum, *Salmonella* and other harmful microorganisms including molds, other bacteria, and even viruses are not effectively killed and may even thrive.

Process times employed at the temperatures just identified in the novel pasteurization processes disclosed herein to meet minimum requirements equivalent to those mandated by the USDA for liquid eggs range from a minimum RPT of about 50 minutes at 130° F. to a minimum RPT of about 4.50 minutes at 139.5° F. The time/temperature parameters taken into account include these factors: (1) the temperatures achieved by all particles in and throughout the mass of a shell egg; the time for which all particles are held at that temperature; and the average time that every particle is heated, assuring that each particle is subjected to at least the minimum conditions needed to guarantee effective pasteurization; (2) the minimum-to-maximum process parameters which will avoid or minimize adverse changes in appearance and performance vs. maximum kill of infections; and (3) the attainment of conditions needed to provide the equivalent of the minimum USDA mandated pasteurization standards for liquid whole eggs.

The initial egg temperature at the beginning of the pasteurization processing of whole shell eggs may range from a low of about 38° F. to a high of about 60° F. with a probable average year around temperature of about 55° F. The average preprocessing temperature should be somewhat lower than 45° F. for whole shell eggs destined for consumer distribution.

Effective pasteurization in accord with the principles of the present invention requires that the preprocessing starting temperature be known. This temperature is used to determine TPT. As suggested above, TPT has two components, EqT time and RPT, with EqT time being the time required for an egg to reach equilibrium with the temperature of the pasteurization medium throughout its mass and especially in its most thermally inaccessible portions such as the center of the yolk. Only after EqT is achieved can RPT, the time at a selected pasteurization process temperature equivalent to that mandated for liquid whole eggs, begin. Once the center of the shell egg is at the selected pasteurization temperature, the egg is processed at USDA-mandated temperatures and times to ensure time-at-temperature compliance at the center of the shell egg yolk with at least the minimum USDA standards for liquid whole eggs. This ensures that, completely throughout its mass, the egg is maintained at a temperature high enough to effect the destruction of harmful bacteria for a time long enough for that goal to be realized.

Examination of FIG. 2 shows the following minimum temperature/time requirements for liquid whole eggs, and those parameters may be applied equivalently to shell eggs once the selected pasteurization temperature has been achieved at the shell egg yolk center. The same data appears in tabular form in Table 1. In each instance, the indicated time is the minimum RPT needed for an acceptable or better kill of harmful microorganisms at the corresponding temperature.

TABLE 1

| Temperature | | Required RPT (min) |
|---|---|---|
| 130° F. | (54.4° C.) | = 65 |
| 131° F. | (55.0° C.) | = 49 |
| 132° F. | (55.6° C.) | = 38 |
| 133° F. | (56.1° C.) | = 28 |
| 134° F. | (56.7° C.) | = 20 |
| 135° F. | (57.2° C.) | = 16 |
| 136° F. | (57.8° C.) | = 11 |
| 137° F. | (57.8° C.) | = 8 |
| 138° F. | (58.9° C.) | = 6 |
| 139° F. | (59.4° C.) | = 4.75 |
| 140° F. | (60.0° C.) | = 3.5 |

When the Table 1 pasteurization time and temperatures are applied to shell eggs, additional, EqT time must be allocated from the time the egg is placed in a heat transfer or pasteurization medium maintained at the desired pasteurization temperature in order for the center of the yolk to achieve EqT—the initial point of RPT and the point at which the egg reaches temperature equilibrium with the heat transfer medium. The RPT for a given pasteurization regime can only begin after this point has been reached and heat has been transferred through the external portions of the shell egg into the center of the yolk such that the temperature at the yolk center and at every other locus throughout the mass of the egg has reached equilibrium with the process medium.

The total time for the entire egg to come to equilibrium with the process medium or reach a predetermined effective process temperature, EqT, added to the real processing time, RPT, as set forth in FIGS. 1 and 2 and Table 1 equals the total processing time, TPT.

Among factors determining the time required to reach EqT are egg size, the preprocess temperature of the egg, and the selected pasteurization process temperature.

For purposes of achieving heat transfer through the shell to the interior of an egg, one liquid (oil, water, glycol or the like) will work about as well as another provided, of course, that the liquids are safe for this use. A gas such as air, humidified air, or air mixed with gases such as carbon dioxide or nitrogen can be used as a pasteurization medium but is not preferred for heating eggs to EqT. Such gases may be used for the RPT phase of the pasteurization process or for TPT processes which involve both EqT and RPT phases. However, for RPT steps, liquids are also usually preferred. The just-identified gases are frequently preferred for tempering, a technique described in detail hereinafter and optionally employed to ensure efficacious pasteurization of eggs in processes employing the principles of the present invention.

It is not uncommon for eggs in a process lot to be at different temperatures. The ignoring of this significant condition can lead to the selection of inappropriate EqT, RPT, and/or TPT time and temperature combinations. Those parameters providing effective, if not optimal, pasteurization of eggs at one initial temperature may result in the cooking of the whites of eggs at a higher initial temperature. Conversely, if the process batch contains eggs with a lower initial temperature, those eggs may not be subjected to the minimum RPT for the selected pasteurization temperature specified in FIG. 2 and Table 1.

Tempering may be employed in accord with the principles of the present invention in instances where disparity in initial egg temperatures is evident or even suspected to eliminate the problems the temperature disparity may cause. Tempering is an initial or pre-processing step in which the eggs are held at a sub-pasteurization temperature long enough for the eggs to all come to the same temperature. This promotes uniformity of results in the subsequent pasteurization of the eggs, significantly reducing or even eliminating the likelihood of there being eggs with cooked whites and/or insufficiently pasteurized eggs at the end of the pasteurization process. Tempering can also be employed to reduce, if not eliminate, thermal shock cracking of the eggs being processed.

Tempering can be carried out in air and other gases. The gas can be dry air or air humidified to prevent evaporative losses of water from the egg during tempering, a phenomenon that is preferably avoided because of the weight loss suffered as an egg dries. An alternative, if the pasteurization process medium is not water, is to add water to that medium to make up evaporative losses during pasteurization by restoring water lost from the egg by evaporation.

The shortest effective tempering times are preferred. It is undesirable to hold the egg at any temperature which favors microorganism growth for any longer than necessary; and the tempering temperature might be one of that character.

The basic shell egg pasteurization process takes into account process steps and factors other than those identified above such as: (1) a normal range of egg sizes at any normal ambient preprocess temperature, tempered or untempered, packaged or unpackaged, or coated; (2) liquid and gas or fluid processing; and (3) the use of turbulence or vibration to promote the transfer of heat into the eggs. The process preferably employs primary pasteurization parameters of >134.5° F. to <139.5° F. (± ca. 0.3° F.) for a TPT of from about 23 to about 56 minutes or, for maximum TPT, pasteurization process temperatures of 130.1° F. to 134.6° F. (± about 0.3° F.) for TPT's of from about 46 to about 345 minutes.

Preferred TPT's and pasteurization temperatures for eggs weighing between 35 and 90 gms and at a normal preprocess temperature between 40° F. and 70° F. are 138° F.±1.5° F. at 44±about 8 minutes. Preferred TPT's for eggs weighing between 50 and 80 gms at preprocess temperatures between 45° F. and 55° F. for pasteurization temperatures of 138° F.±0.75° F. are about 44±5 minutes. These time and/or temperature ranges are modified, using test data and routine trials, when intermittent temperature pasteurization as described in succeeding paragraphs of this specification is employed.

There are important versions of the invention in which heating of the egg is accomplished in stages with one or more of the heating steps being followed by a dwell time in which the temperature equilibrates throughout the interior of the egg.

Another, somewhat similar approach is pasteurization in stages with substantial dwell times between the stages. Tests have demonstrated that pasteurization within the ranges of time/temperature parameters described above followed by a second pasteurization treatment may be synergistically effective to provide longer shelf lives.

Because of the virtually unlimited number of options this offers, it is impractical to list the parameters for each and every option. Furthermore, this is unnecessary; the parameters appropriate for a particular option employing intermittent or discontinuous heating can be readily and routinely determined because the critical criteria are known. Specifically, the pasteurization temperature and RPT must be such that, at the end of the pasteurization process, all particles throughout the mass of the egg will have been heated at the selected pasteurization temperature for an RPT equivalent to at least the minimum mandated by a USDA Standard for liquid whole eggs (FIGS. 1 and 2 and Table 1).

Like pasteurized eggs and egg products, a shell egg processed by time-at-temperature pasteurization will typically suffer some diminution of overall sensory properties and some loss of functionality. Generally, in processing shell eggs in accord with the principles of the present invention, any quantitative changes resulting from implementation of the invention under the less extreme process conditions are not noticeable by a consumer of average sensitivity. Under extreme conditions, such as pasteurization at a temperature of 131° F. for 100 to 240 minutes, products which may have some average-consumer-noticeable differences may be produced. For example, a shell egg processed by the foregoing regime will have what appears to be a larger yolk than a control. This is thought to be due to egg lipids thinning and running under the prolonged influence of the process heat, thereby exerting greater hydraulic pressure against the vitelline membrane which contains the yolk matter. The membrane is comprised of protein and consequently can relax and stretch. This condition does not correct itself when the egg is cooled to ambient or to refrigeration temperatures. Without the control for comparison, the enlarged yolk may be noticeable only because it will lay flatter in a pan than a non-pasteurized egg, for example.

While possibly inconvenient, this consumer noticeable fault is minor when compared to the improved food safety of the egg. Nevertheless, more moderate or optimal process conditions such as pasteurization at 138° F. for about 40 to 46 minutes TPT will typically be employed. This yields products which are superior in that they are difficult to differentiate from controls in any qualitative factor.

As with pasteurized liquid whole eggs, some loss of functionality in an egg processed in accord with the present invention will be noticed by a baker. However, the difference can usually easily be made up by small increases in the total amount of egg that is used. This potential diminution of functionality is more than offset by the improved food safety.

TPT may be reduced by introducing turbulence into the pasteurization medium and/or by subjecting the shell eggs to mechanical vibration. Both of these mechanisms—a turbulent pasteurization medium and the application of vibrational energy to the egg—increase the rate of transfer of heat from the pasteurization medium to the interior of the egg. Thus, while not essential, the utilization of turbulence and vibration can result in more effective treatment regimes. A turbulent pasteurizing medium or vibration of the egg should be used where the additional benefits of quicker, more effective processing are desirable.

Ultrasonically induced and other forms of vibration including those produced by cavitation may also be employed to advantage in the microorganism destroying treatment. Such vibration, like that of the mechanical variety, promotes the transfer of heat through the shell and throughout the mass of the egg. This enhances process effectiveness, ensuring more efficient reduction of infectious microorganisms.

Other, advantageous process techniques are deliberate overshooting of the selected treatment temperature when the egg is initially heated and the pulsing or alternating of the treatment temperature between two different levels.

Heating shell eggs and subsequently holding them at selected temperatures for an appropriate time to effect pasteurization is preferably followed by rapid cooling (or quenching) of the treated eggs. This final step ensures that, as they are cooled, the treated eggs pass rapidly through that portion of the temperature spectrum favoring bacterial growth. If quick cooling is not employed, any remaining harmful bacteria may multiply and negate some or all of the effects of the time-at-temperature treatment, especially if the eggs are allowed to remain for any significant time in a temperature zone favoring microbial growth. For this reason, natural cooling of treated eggs to ambient conditions or even cold storage conditions can allow new growth of any remaining unkilled microorganisms to occur.

Even rapid cooling can have serious drawbacks since microorganisms in the ambient environment of the treated eggs can recontaminate the egg surface and be drawn back inside through shell pores by negative pressure generated inside the shell as the egg cools. Therefore, the more rapid the cooling, the cleaner the environment, and the more sterile the cooling environment, the better.

The best possible way to avoid recontamination of the pasteurized eggs by contact with organisms in the ambient environment, by handling, and by other mechanisms is to package the egg in an impervious film or other package prior to cooling. Examples of appropriate films and package materials are those fabricated of polyethylenes and polyvinylchlorides. Other acceptable packaging which can be used to prevent recontamination includes composite films and readymade, food approved proprietary packaging such as Cry-O-Vac®, Seal-A-Meal®, and the like.

The egg may be processed in the package and the package aseptically sealed after processing, but before cooling; or the package may be sealed prior to pasteurization processing, this being followed by cooling to ambient or a refrigeration temperature. Among the advantages of processing the egg in packaging is that no recontamination can occur during steps requiring cooling or handling. The packaging of eggs before processing, particularly by the dozen or in the other multiples, offers many other advantages including the ability to use modified atmosphere gases such as carbon dioxide, nitrogen, and mixtures as a package filler to: prevent spoilage; reduce breakage during processing; make handling, the automation of production, and standardization of egg moisture levels easier; and facilitate the addition and the diffusion into the egg of process aids such as organic acidification agents including citric, lactic, benzoic, and ascorbic acids, to name but a few. Eggs processed in individual packaging may be slipped into more-or-less standard egg cartons while packages in which eggs are processed in multiples may be wrapped or placed in cardboard sleeves to present the packaged appearance commonly expected by the consumer.

Packages may be filled with carbon dioxide, nitrogen, or a carbon dioxide/nitrogen mixture before pasteurization or after pasteurization and before cooling and then sealed. Upon cooling in the sealed package, the gas will be drawn in through the pores in the egg shell and the shell and vitelline membranes to provide a stabilizing, deterioration inhibiting gas inside the egg.

Storage at acceptable elevated temperature for short durations can be used to effectively pasteurize eggs. Critical parameters for such storage pasteurization are temperatures of ca. 131° to 135° F. (±1° F.) for from about 42 minutes to as long as 390 minutes using water—e.g., in the form of a spray—as a heat transfer medium. Very high humidity air; i.e., air with a relative humidity $\geq 85\%$ can also be employed as a heat transfer media with the process times then ranging from about 50 minutes to 400 minutes. Prepackaging of the eggs before processing is preferred in this type of pasteurization process due to the many advantages heretofore mentioned.

The important objects, features, and advantages of the invention will be apparent to the reader from the foregoing and the appended claims and as the ensuing detailed description and discussion proceeds in conjunction with the accompanying drawings.

BRIEF DESCRIPTION OF THE DRAWINGS

FIGS. 13–17 are schematic views of five other systems for processing whole shell eggs in accord with the principles of the present invention.

DETAILED DESCRIPTION OF THE INVENTION

Figure 3:
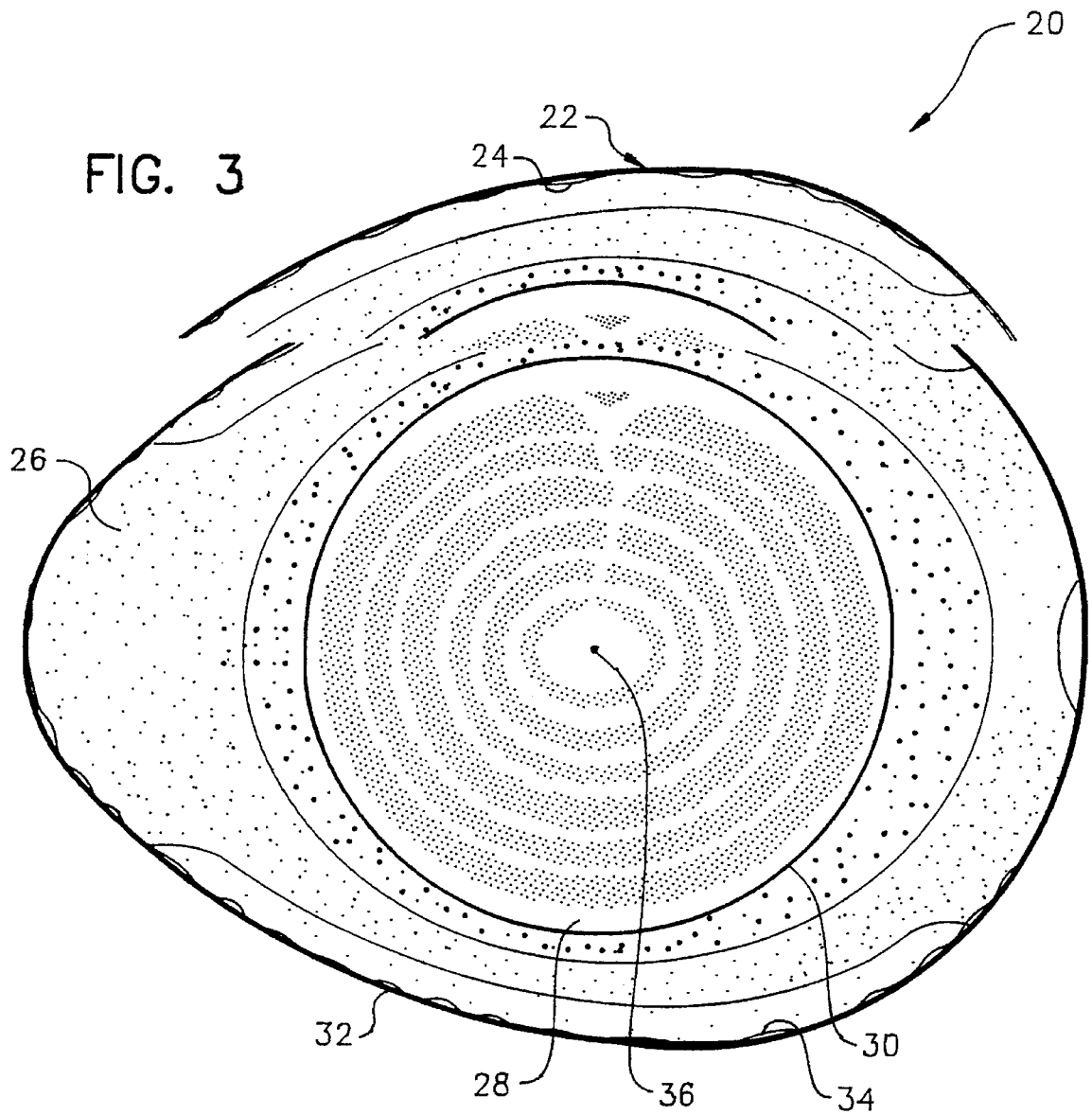
FIG. 3 is a pictorial cross-section through a whole, uncooked, poultry, shell egg.

Referring now to the drawings, FIG. 3 depicts a whole, uncooked, poultry egg 20. From outside to inside, egg 20 includes: (1) an egg shell 22; (2) outer membranes which are attached to the inner side of shell 22, include a shell membrane and an egg membrane, and are collectively identified by reference character 24; (3) viscous layers of albumen collectively referred to as the egg white and identified by reference character 26; (4) a liquid yolk 28; and (5) the vitelline membrane 30 which is thin and relatively strong and surrounds and envelops egg yolk 28. Additional information on the structure of poultry egg components, their functions, and attributes is found in THE AVIAN EGG CHEMISTRY AND BIOLOGY, Burley et al., John Wiley & Sons, Inc., New York, N.Y., 1989, which is hereby incorporated by reference and which may be referred to by the reader if desired.

Heretofore proposed time and temperature pasteurization techniques for poultry eggs focus almost exclusively on the destruction of superficial infections on the outer and inner surfaces 32 and 34 of egg shell 22. An exception is found in Funk U.S. Pat. No. 2,423,233 which purports to disclose—but does not document—time and temperature pasteurization processes which are capable of destroying infections present in the white of a poultry egg. Nothing found to date discloses time and temperature pasteurization processes capable of destroying infections in the yolk of a poultry egg, let alone those at the very center 36 of a yolk such as depicted at 28 in FIG. 3. In fact, when applied to a shell egg which is infected throughout its mass or primarily in its yolk, all known shell egg pasteurization processes are: insufficient to meet minimum effective standards such as those established for liquid eggs; accomplish nothing; or create conditions which are actually conducive to, and frequently optimal for, the increase of food poisoning infections already present in the shell egg.

Infections of the shell egg may be commonly found: (1) concentrated at or in close proximity to the egg shell/egg white interface as a result of migration through the pores of the shell and the outer membranes; (2) indigenous and scattered throughout the mass of the egg; and (3) indigenous but concentrated in the center and other areas of the yolk. Indigenous infections may be a result of: transovarian infection of the yolk, through-the-pore contamination, and generalized infection. While it is convenient to think in terms of *Salmonella* which almost seems to be symbiotic with poultry and egg products, it is also likely true that eggs serve as rich host media for infectious organisms of all sorts under some circumstances.

As discussed above, to meet at least the minimum standards of pasteurization mandated by the USDA for liquid eggs and to retain or enhance the appearance of freshness, functionality, and organoleptic properties, very specific combinations of times and temperatures must be employed. These time and temperature combinations take into account the smallest to largest commercial egg sizes; starting temperatures ranging from 40° to 70° F.; unpackaged processing without process aids or augmentation such as by overshooting and flash tempering; and water as the heat exchange media. The process parameters preferably range from: (a) a minimum TPT of about 34 to 52 minutes at 138.9° F.±0.5° F. to (b) about 75 to 400 minutes at 130.3° F.±0.4° F. Preferred process parameters for shell eggs at a representative 45° F. starting temperature are:

TABLE 2

| Weight (gms) | Temperature (°F.) | TPT (min) |
| --- | --- | --- |
| 40–60 | 138.5 ± 0.7 | 40–46 |
| 60–80 | 138.0 ± 0.5 | 42–48 |

In many cases, the initial temperature of the eggs being processed will be below the nominal cold storage temperature of 40° F., above the nominal room temperature of 70° F., or at a level between those two nominal temperatures. For example, cold storage eggs left on a loading dock in freezing weather may have an initial processing temperature which is less than 40° F. In those cases, minimum, maximum, and optimal processing times can be extrapolated from the temperatures set forth above, derived by the routine testing of appropriately sized samples, or be derived through a combination of extrapolation and testing steps to determine the EqT time of the eggs and the TPT required to provide the desired RPT.

Holding a shell egg under selected time and temperature conditions as specified above can achieve minimum USDA liquid egg pasteurization standards and can effect significant reductions in, if not entirely eliminate, infections and still yield a consumer acceptable shell egg.

It is entirely practical to process eggs by the novel techniques disclosed herein in lots and to employ in the practice of the present invention continuous techniques similar to some already in use by the egg industry; e.g., continuous egg washing machines, which can clean hundreds of thousands of eggs per day. In such applications, it is commonly impractical to control process temperatures to small fractions of a degree. Consequently, except for processing steps of very short durations, temperatures of less than 139.5° F. are more practical pasteurization temperatures.

In any event, it is essential that the pasteurization process time and temperature be such that the shell egg, throughout its mass including the center of the yolk and other innermost parts of the egg, reach and be maintained at a pasteurization temperature for a RPT equal to at least the minimum USDA required for liquid eggs irrespective of the size, preprocess temperature, freshness, shell thickness, or other characteristic of the egg or the heat transfer medium in which or specific process by which the egg is processed.

The eggs may be treated or processed in accord with the principles of the present invention in any gaseous liquid or fluid, food grade heat transfer medium including air, other gases such as those discussed above, oil, a glycol, or water.

In those tests described in the examples which follow, counts of infections were made with PETRIFILM® aerobic count plates, using the protocol described in the PETRIFILM® Interpretation Guide, with a Millipore® sampler using the protocol described in the instructions for using that product, or with an equivalent device and protocol.

Figure 9:
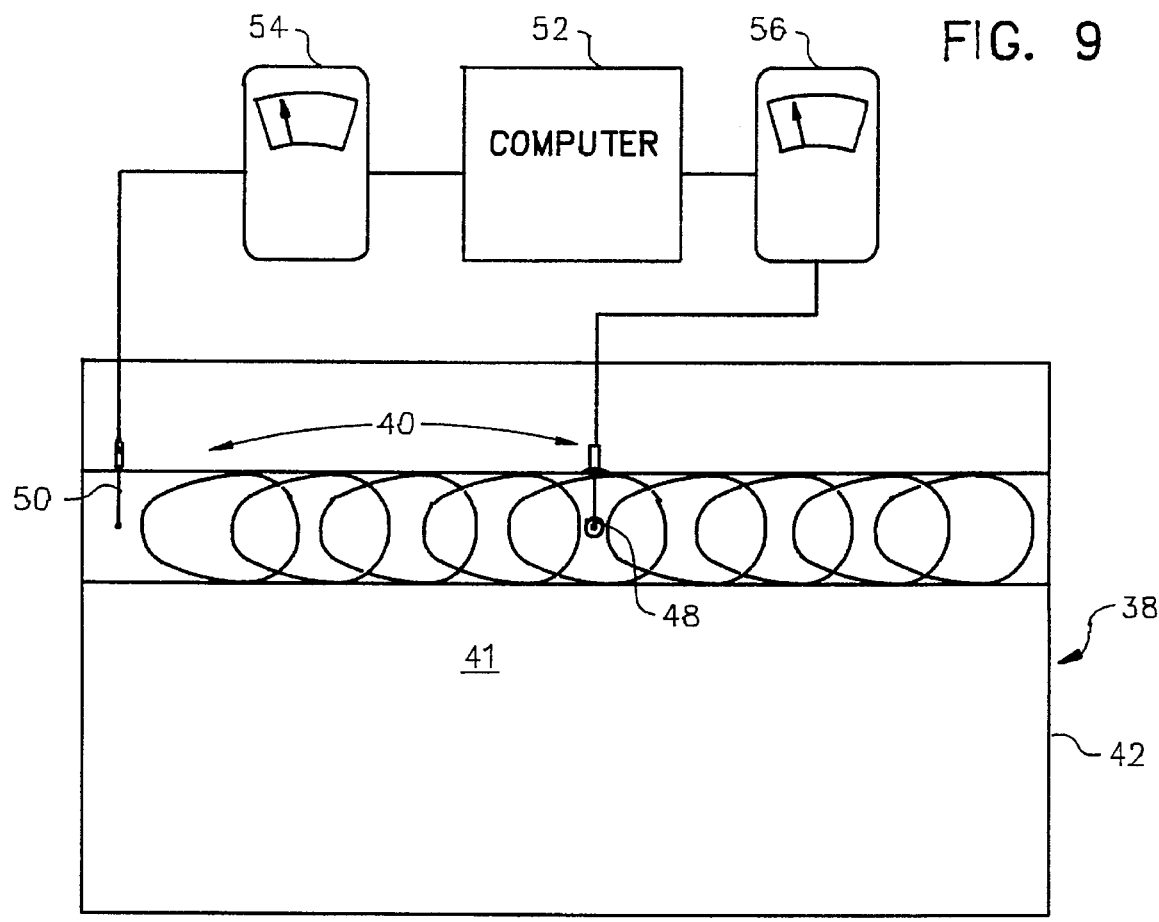
FIGS. 9 and 10 are diagrammatic side and plan views, respectively, of one system which can be employed to pasteurize process poultry shell eggs in small lots in accord with the principles of the present invention.
Figure 10:
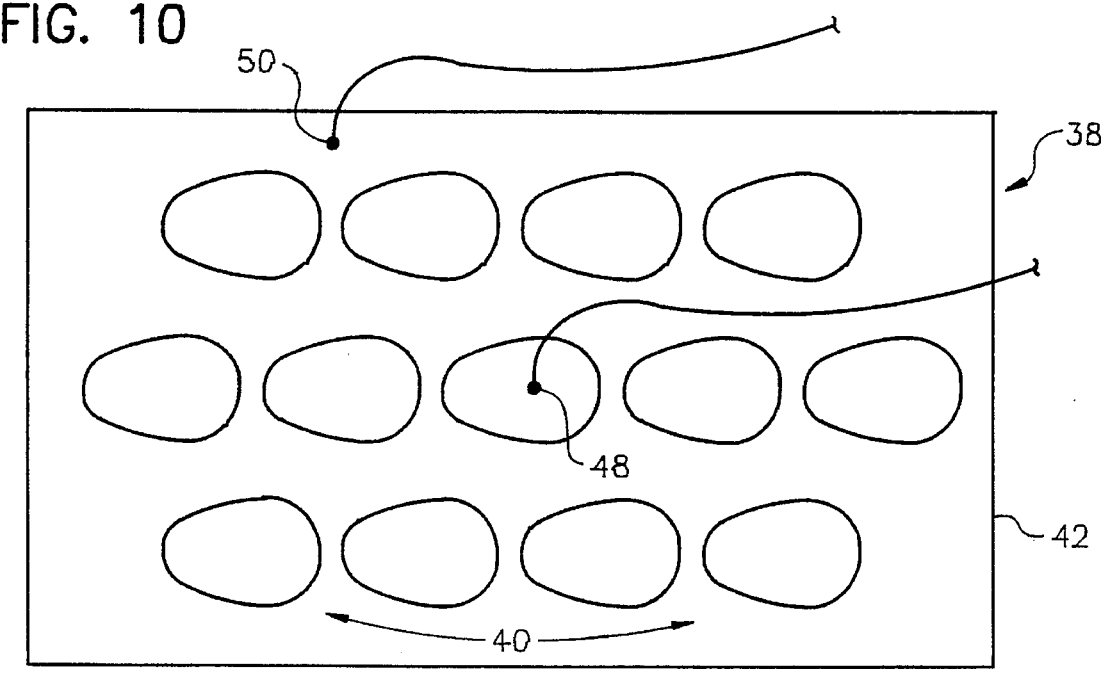

The equipment for the tests described in the bulk of the examples is shown diagrammatically in FIGS. 9 and 10. It included a Blue M MAGNAWHIRL precision water bath 38 with controls (not shown) which allow the temperature of the bath to be adjusted. A batch 40 of eggs to be processed was placed in the body of water 41 filling the tank 42 of the Blue M apparatus, typically although not always in batches of 13 arrayed as shown in FIG. 10. Gentle (laminar flow) circulation of the water 41 in tank 42 was employed to eliminate temperature gradients and thereby ensure that all of the eggs in the body of pasteurization water were heated in the same, uniform manner.

The temperature at the center of the yolk of that egg 46 in the center of the batch 40 was measured with a Type K thermocouple 48 at the center of the yolk. A reference thermocouple 50 placed in the body of water 41 in tank 42 was used to measure the temperature of that pasteurization medium. Because of the uniformity of the pasteurization conditions, the center-of-yolk temperatures of the remaining eggs in a batch 40 were assumed to be the same as the temperature measured by thermocouple 48.

Thermocouple 48 was installed by puncturing the shell, outer membranes, and vitelline membrane (or yolk sac) of egg 46 with a hypodermic needle. The thermocouple 48 was then introduced with its progress being observed through a candling slit, allowing the insertion of the egg to be stopped precisely when the temperature sensing tip reached the center of the egg yolk. Epoxy resin was then applied to the shell of the egg to seal the puncture in the shell and to fix the thermocouple 48 in place.

The center-of-yolk temperature of egg 46 and the bath temperature were continuously monitored, using a personal computer 52 running Quick Log PC software supplied by Strawberry Tree of Sunnyvale, Calif. and Tegam K, J&T, single input thermometers 54 and 56.

In many of the tests described in the examples, the eggs were inoculated with an infectious organism. The number of organisms stated in the example is the number per gram of egg weight.

EXAMPLE I

Any shell egg subjected to the Funk devitalization process is initially at an ambient temperature typically ranging from about 45° to 55° F. The preferred Funk TPT's and temperatures (5 to 10 minutes at 138° F. and 130° F. for 20 to 40 minutes) cannot provide any RPT in the yolk of an infected egg as demonstrated by the following tests.

TEST 1

Funk Preferred TPT/Temperature of 138° F., 5 to 10 Minutes.

Method

Shell eggs were pasteurized at Funk's preferred TPT and temperature. The eggs had an average size of 60 gms and were at an improbably high pre-process temperature of 70° F. They were processed in the Blue M precision water bath with the water agitated under laminar flow conditions to provide uniform heating (a favorable equivalent of Funk's "rotation").

Results

Figure 4:
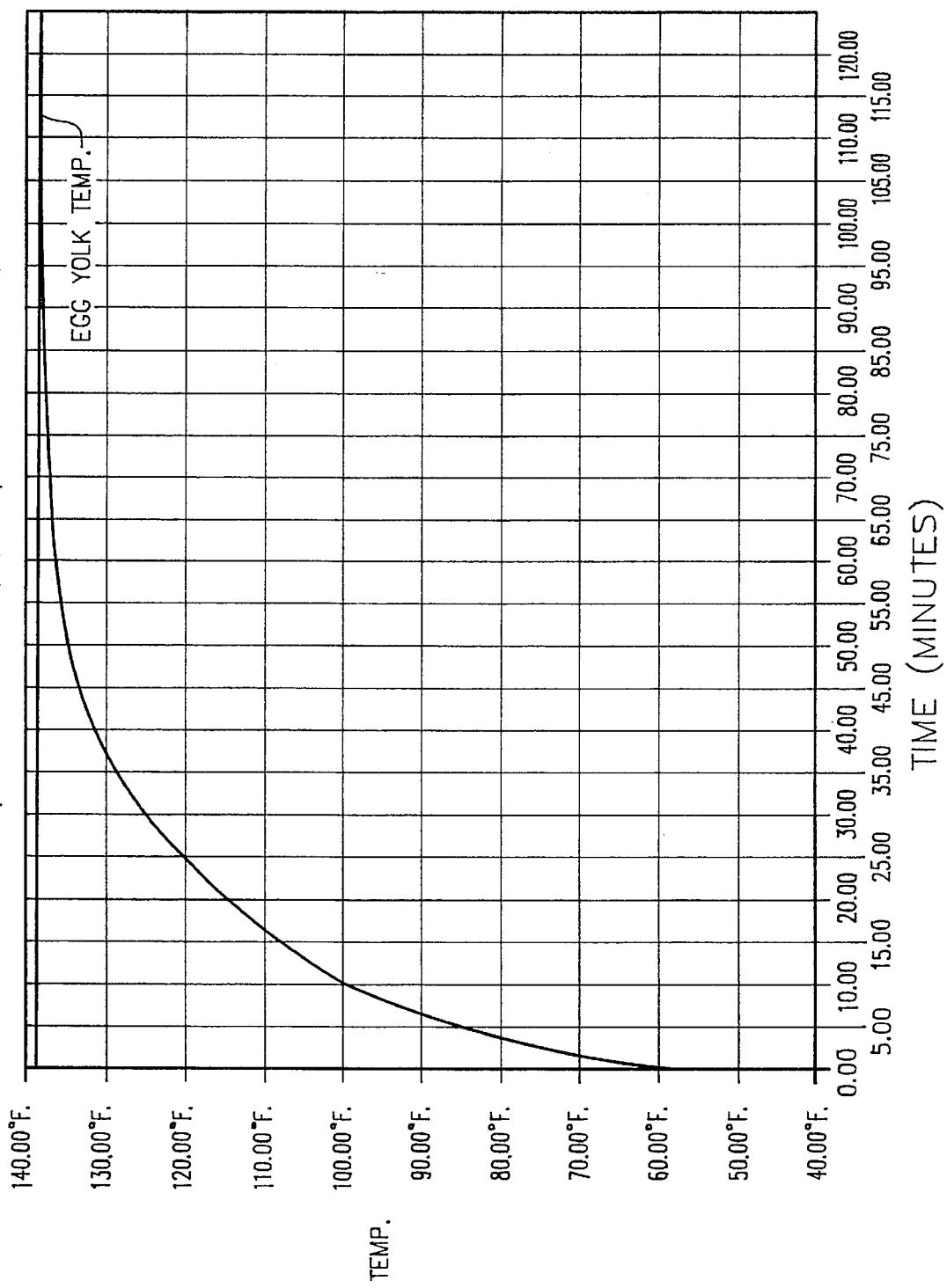
FIGS. 4–8 are charts showing the temperatures reached after TPT's of zero to 120 minutes at the center of shell eggs processed in water baths with temperatures of 138°, 132°, 134°, 136°, and 140° F.
Figure 5:
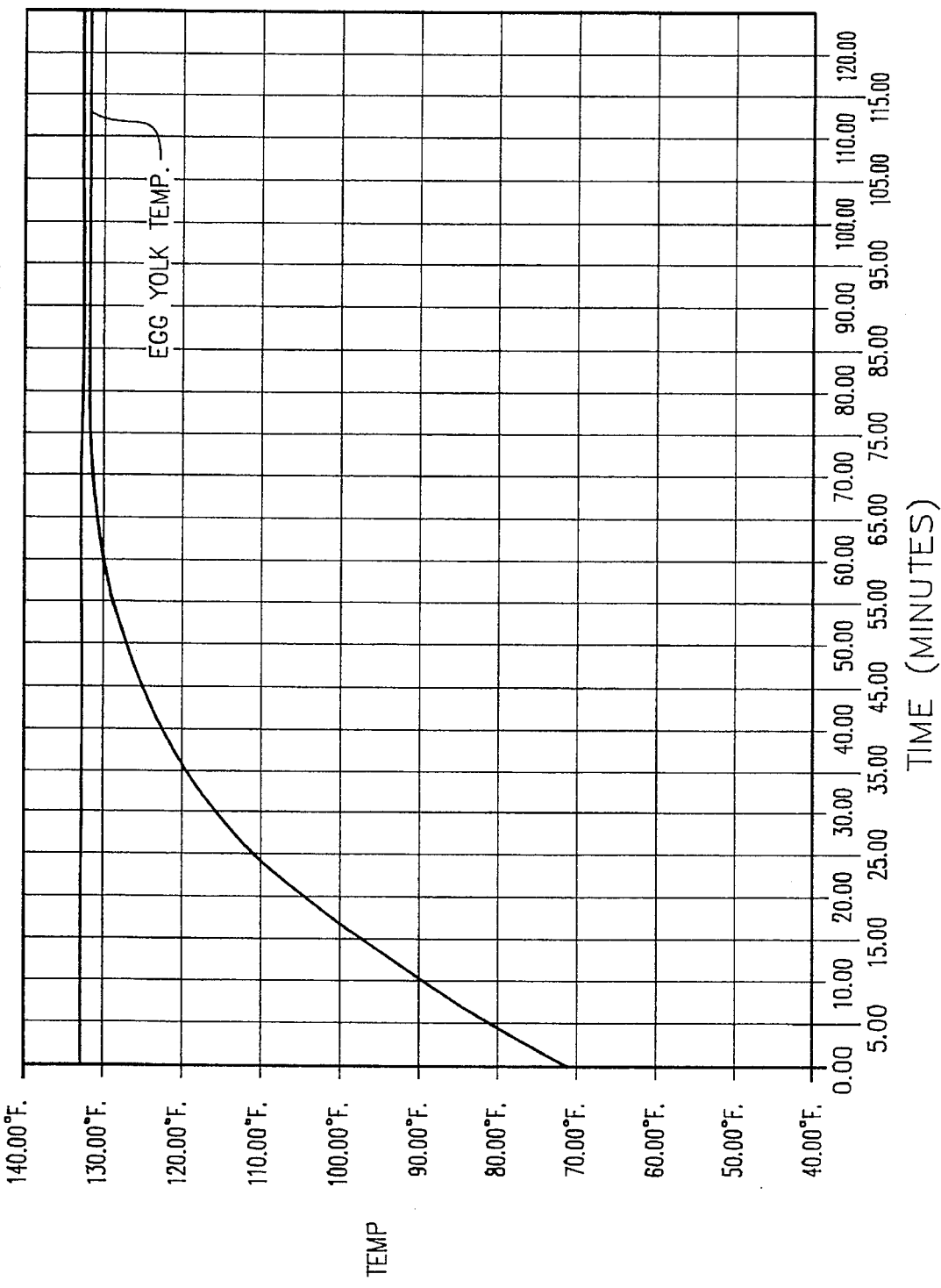
Figure 6:
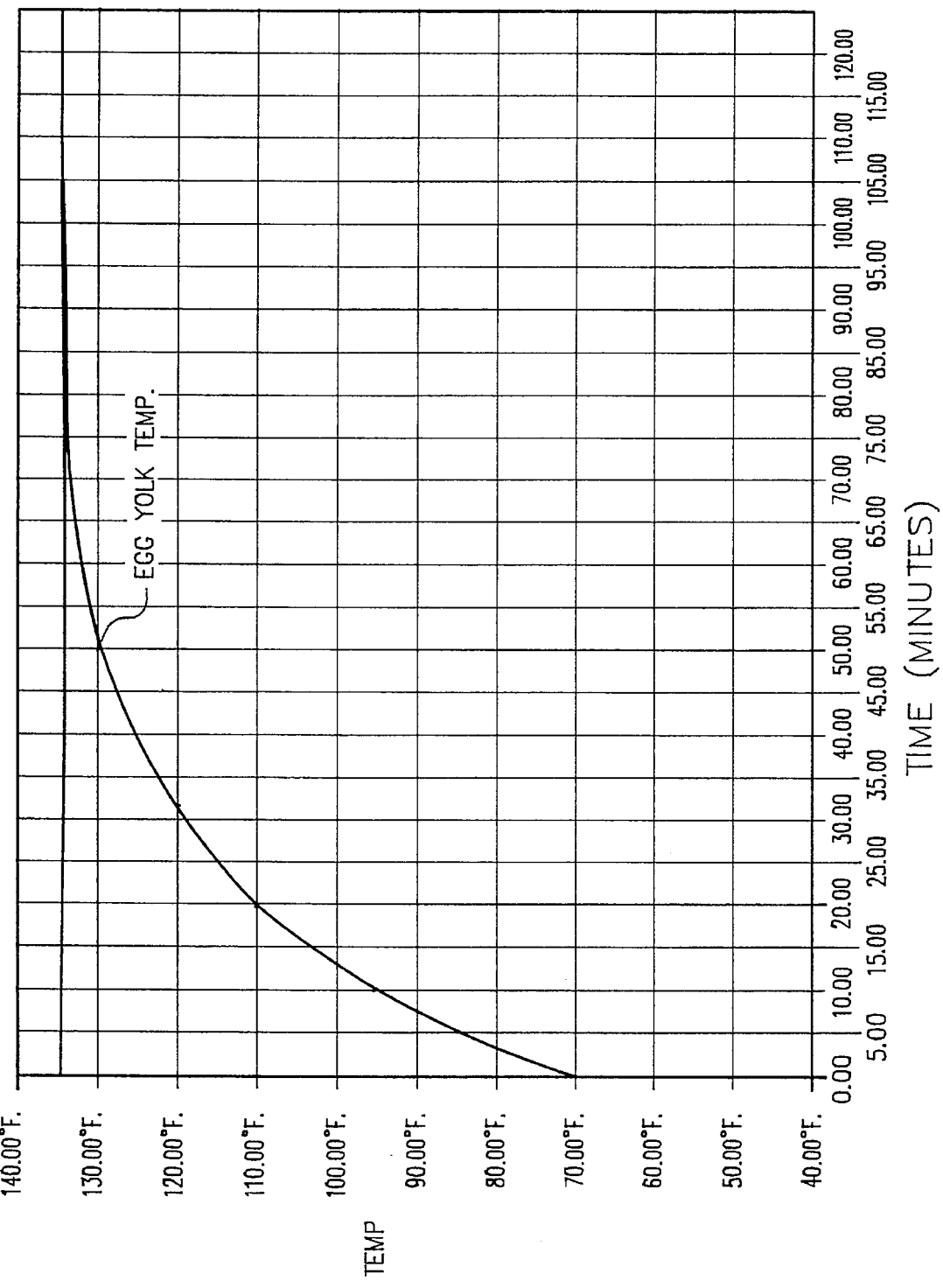
Figure 7:
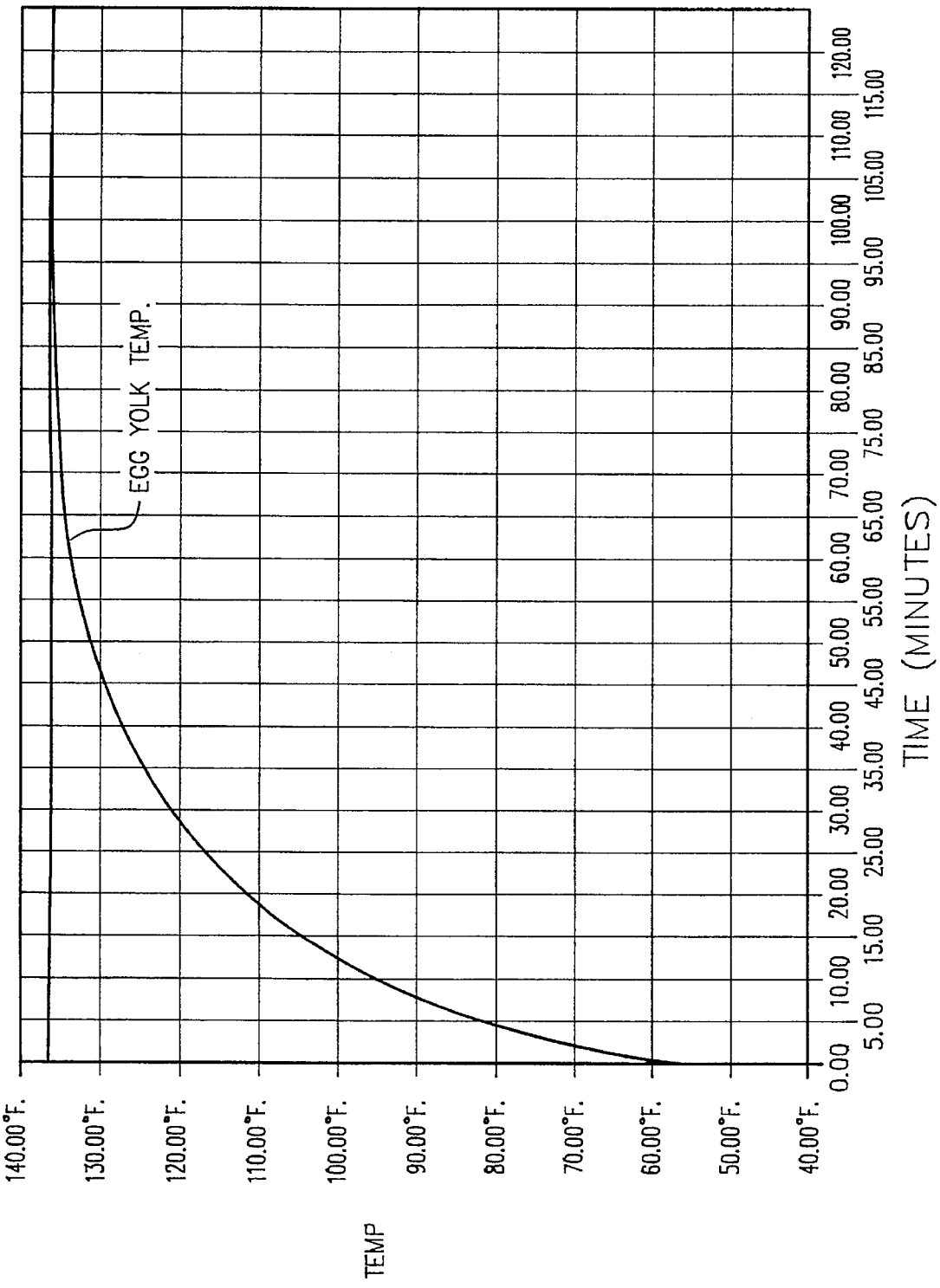
Figure 8:
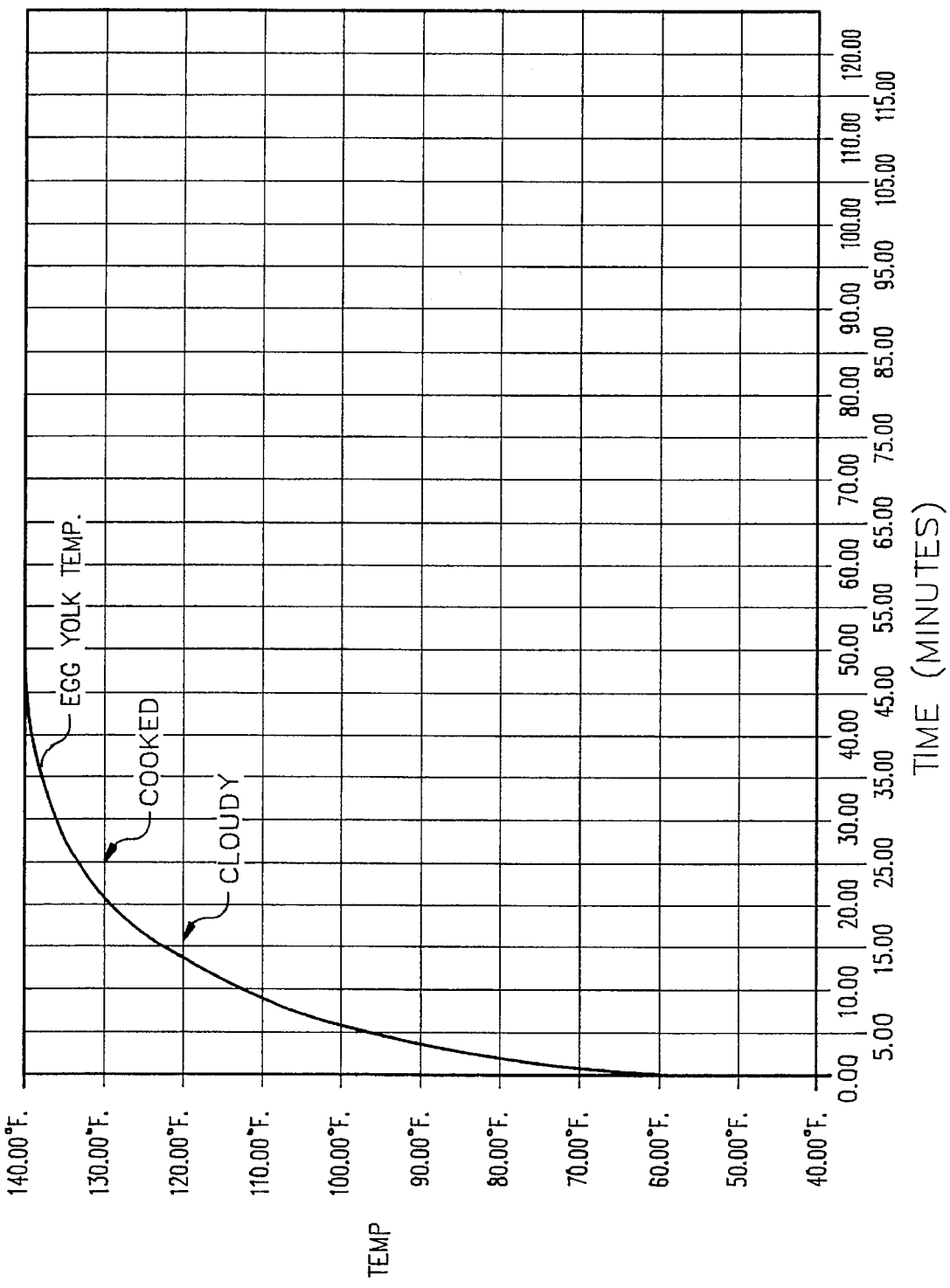

After 5 minutes, a yolk center temperature of only about 93° F. was reached (see FIG. 4). This is nearly the optimal growth temperature for most *Salmonella* sp. (98.6° F.).

After 10 minutes, the yolk achieved momentarily a temperature of about 125° F., still in the temperature range in which microorganisms actively grow.

Comments

If the yolk of the egg processed in this manner happens to be infected with *S. enteritidis*, for example, such treatment will in effect represent exposure of the infected egg to active infection growth conditions (>~70° to <~120° F.), including some exposure at optimal growth conditions (>~95° to <~105° F.) with absolutely no exposure to effective killing conditions (>~129° to 160° F. for at least 3.0 minutes).

Conclusion

Eggs processed according to Funk's preferred TPT/Temperature conditions can only result in increased severity of any food poisoning infections, except superficial ones.

TEST 2

Funk Preferred TPT/Temperature of 130° F., 20 to 40 Minutes.

Method

Same method as in Test 1 except that the eggs processed in the most favorable of all possible Funk TPT/temperatures combinations—130° F. for 40 minutes.

Results

Starting at the very favorable but improbably high starting temperature of 70° F., the center of the egg yolk reached a temperature of only 130° F. (after ca. 36 minutes). That is, it took 36 minutes to reach EqT and initiate RPT.

Comments

This leaves a RPT of only four minutes before Funk's mandated maximum of 40 minutes TPT is reached. That RPT of 4 minutes at 130° F. is not nearly long enough to pasteurize the egg to a level equivalent to the most minimal USDA liquid egg standard.

Figure 1:
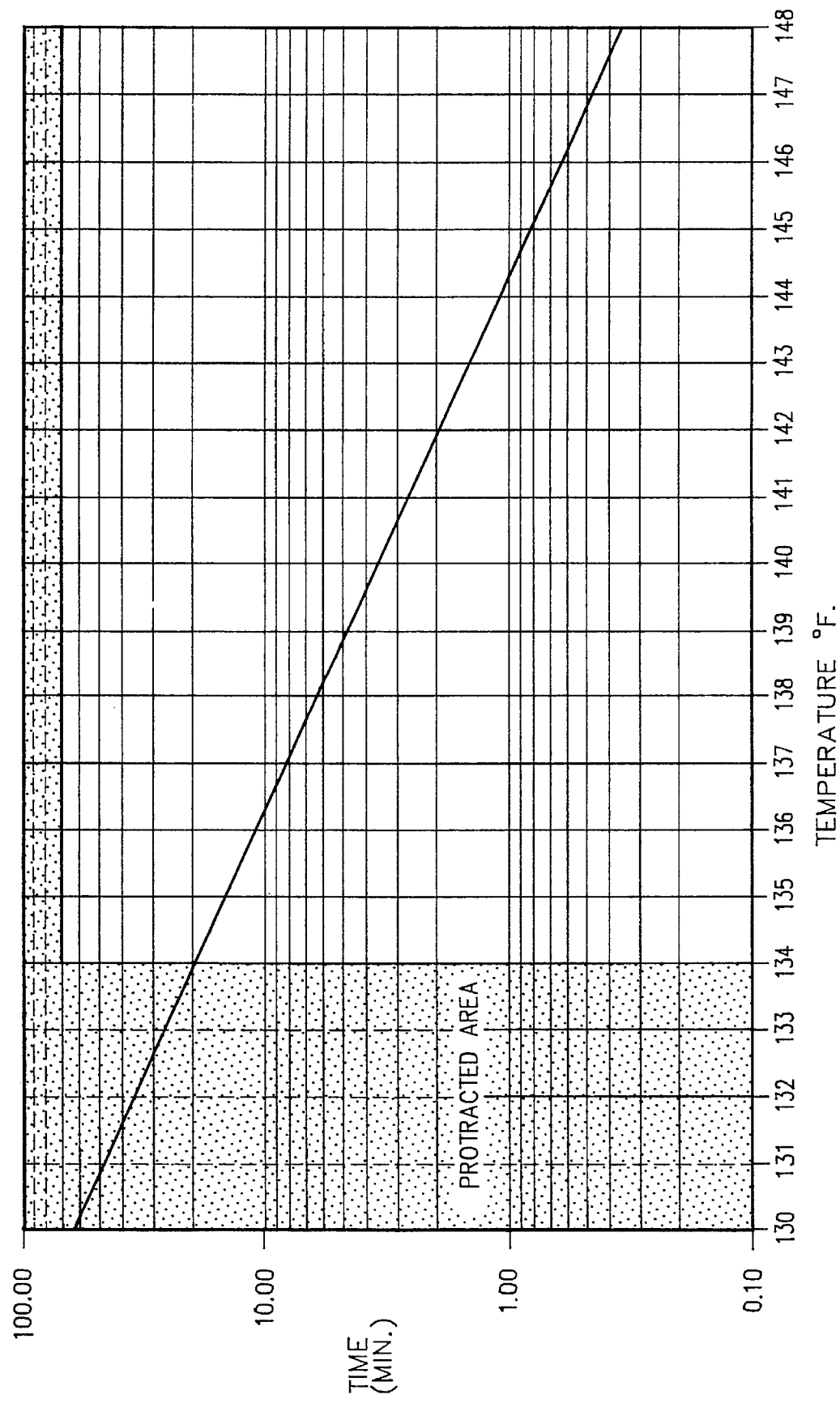
FIG. 1 is a chart depicting the USDA Protracted Whole Egg Standard for pasteurizing liquid whole eggs.
Figure 2:
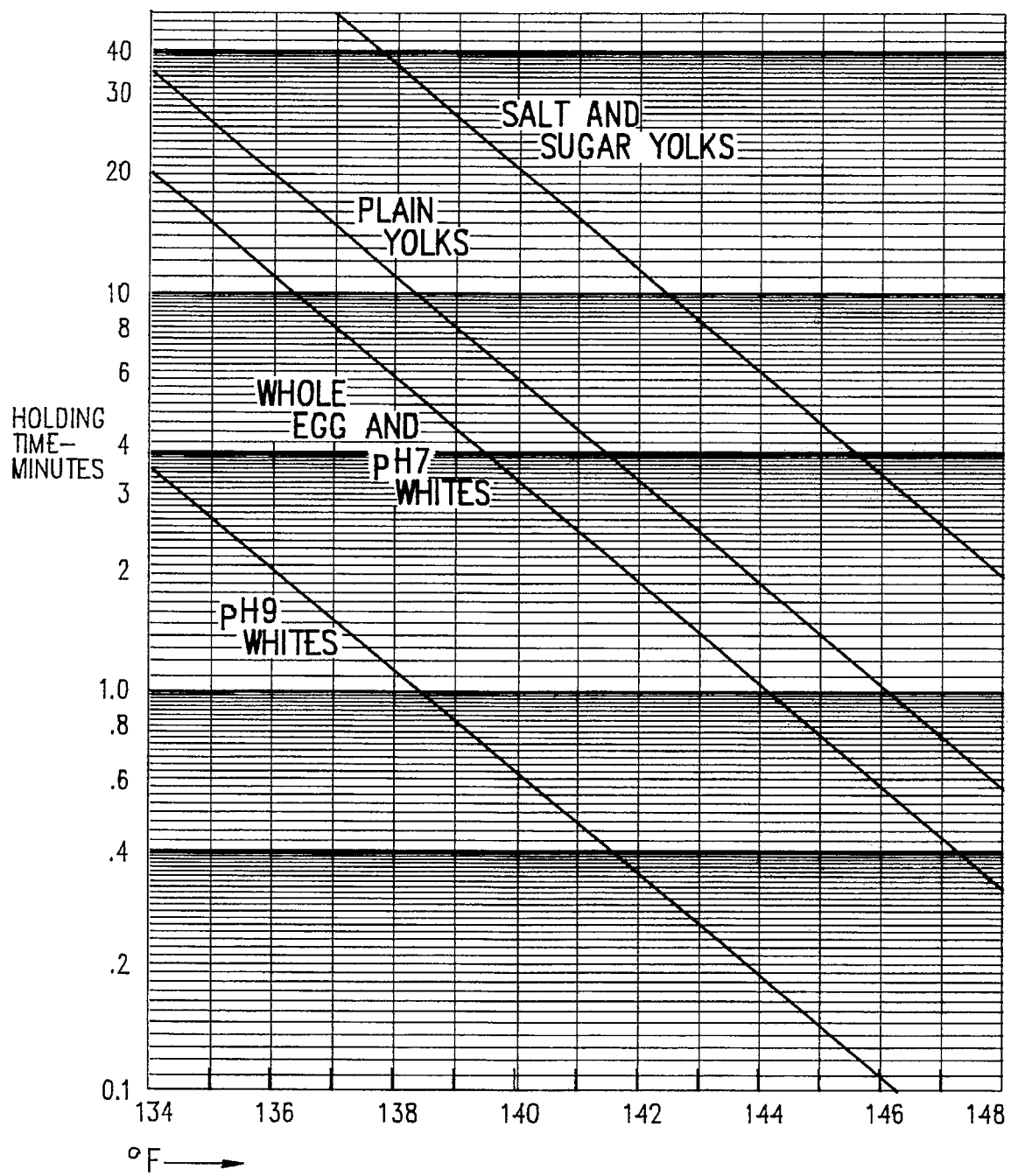
FIG. 2 is a chart showing the minimum conditions mandated by the USDA for pasteurizing liquid whole eggs and other liquid poultry egg products.

Even at a processing temperature of 138° F. an egg acquires an initial temperature throughout its mass which is effective to destroy infectious microorganisms of about 129° to 130° F. only after 36 to 37 minutes. After an additional x minutes (the total RPT), the average of all temperatures over the RPT can be compared to the extended chart of FIG. 2 to determine if minimal process values have been satisfied. Clearly, a total RPT of 4 minutes even at 138° F. is not nearly long enough to pasteurize the egg to a level equivalent to the minimum USDA liquid egg standard.

With the center of the egg yolk reaching 130° F. at the 36th minute and 132° F. at the 40th minute, additional time at temperature would be required for the average temperature to achieve a time at temperature equivalent of the minimum USDA standards shown in the USDA chart.

At least a 50 percent greater RPT of 6 minutes is required at a 138° F. pasteurization temperature to ensure the destruction of infectious organisms throughout the mass of the egg. A far longer time would be required if the temperature at which the egg is heated were only 130° F.

Ignoring Funk's preferred TPT/temperature combinations and sorting through a multitude of possible permutations of other possible Funk TPT/temperature combinations leads to the inevitable conclusion that the most efficacious probable selections fail by significant margins to achieve any meaningful RPT with respect to meeting minimum USDA standard requirements. The many other possible combinations of from 5 to 40 minutes at a temperature in the range of 110° to 140° F. in a majority of cases can only worsen an infectious condition in an egg.

TESTS 3-6

The test was repeated, using water bath temperatures of 132° F., 134° F., 136° F., and 140° F. In the first three of these tests the center of the egg yolk never reached the 130° F. minimum necessary to achieve any RPT whatsoever in Funk's maximum 40 minute TPT (see FIGS. 5, 6, 7, and 8).

Comments

The sixth—140° F. bath temperature test—confirmed that eggs cannot be time-at-temperature processed at a temperature of 140° F. or higher but must be processed for the appropriate RPT at a temperature below 140° F. While the egg achieved initial RPT at 21 minutes of TPT, it also became cooked at a TPT of 25 minutes or after a RPT of only 4 minutes at an averaged temperature of between 130° and 133° F. at the yolk center. The whites of the eggs processed at this temperature were clouded even before the minimum effective EqT of 130° F. was reached, and the eggs were cooked only a few minutes after the minimum 130° F. EqT was reached (see FIG. 8). Clouding and cooking respectively occurred at TPT's of ca. 8 and 24 minutes, both well short of the maximum 40 minutes TPT which the Funk patent disclosure embraces.

Conversely, the 5 minute TPT taught by Funk to be satisfactory is equally ineffective. In none of the tests (132°–140° F., FIGS. 4–8) did the centers of the egg yolks reach the minimum 130° F. temperature required for microorganism destruction in the Funk-specified 5 minute TPT.

One can only conclude that Funk does not make obvious to one of ordinary skill in the art the time and temperature combinations required to pasteurize shell eggs to a level required for food safety; i.e., to even the minimum level mandated by the USDA for liquid whole eggs.

EXAMPLE II

Two dozen fresh shell eggs at 40° F. (4.4° C.) were placed in a 2-gallon, controlled temperature, water bath preheated to 134.6° F. (57° C.).

Two dozen fresh shell eggs at 40° F. (4.4° C.) were placed in a 2-gallon, controlled temperature bath filled with peanut oil. The temperature of the bath was preset to 134.6° F. (57° C.).

At 5 minute intervals, eggs were punctured with a stem thermometer while still in the bath to determine the temperature at the center of the egg. At 5 minutes, the center-of-yolk temperature of the eggs in both baths still averaged only 40° F. (4.4° C.). At 10 minutes, that temperature of the eggs from both baths averaged 47° F. (8.33° C.). The 15 minute average for both batches was 67° F. (19.44° C.). At 20 minutes, the average temperature was 82° F. (27.78° C.). At 25 minutes, it was 98° F. (36.67° C.). At 30 minutes, the average was 113° F. (44.99° C.). At 35 minutes, the average temperature was 121° F. (49.44° C.). At 40 minutes, the average was 129° F. (53.89° C.). At 45 minutes, the average temperature was 134° F. (56.67° C.).

The target temperature at the center of the eggs of 129.9° F. (54.4° C.) was achieved at a time between 40 and 45 minutes. The eggs held for this period of time showed no signs of occlusion of the white. Indeed, the white had thickened, making the egg appear fresher.

This phenomenon of the egg white thickening without occlusion continued until about 1.5 hours had elapsed at which time a very slight but noticeable occlusion of the white appeared. The appearance of the egg was very similar to that of a freshly laid egg, which has a somewhat lightly occluded white.

The bunch-up of the white around the yolk and the disappearance of thin running egg white continued up to 1.75 hours after which the egg became more noticeably occluded.

Eggs which had been held for 1.5 hours at 134.6° F. (57° C.) were equivalent to shell eggs held at 139° F. (59.4° C.) for 1.25 hours. The raw eggs were tested by a panel for appearance and were then prepared by frying, scrambling, and poaching and tested for taste against controls. No significant differences were detected.

EXAMPLE III

Shell eggs for this test were selected for obvious surface filth; i.e., fecal matter, blood streaks, smudges, feather adherence, and the like. Eighteen medium sized eggs selected from several thousand were rinsed in a 0.005% chlorine water solution. The eggs were immersed in a water bath preset to 139° F. (59.4° C.). Every 5 minutes, while still in the water bath, the shell of an egg was punctured and a thermometer inserted into the center of the yolk. The egg was then removed, the shell was broken, and the egg was dropped into a Petri dish for examination and preparation of culture samples.

The results after culturing for the indicated number of hours are shown in Table 3.

TABLE 3

| Condition | | Temperature | Millipore Culture Results (microorganisms per cc) |
|---|---|---|---|
| 5 mins | White clear | Yolk/38° F. | <50/48 hrs |
| 10 mins | White clear | Yolk/39° F. | <100,000/48 hrs |
| 15 mins | White clear | Yolk/51° F. | 0/48 hrs |
| 20 mins | White clear | Yolk/74° F. | <9,000/48 hrs |
| 25 mins | White clear | Yolk/88° F. | <100/48 hrs |
| 30 mins | White clear | Yolk/101° F. | <50,000/48 hrs |
| 35 mins | White clear | Yolk/117° F. | <200,000/48 hrs |
| 40 mins | White clear | Yolk/129° F. | <50/48 hrs |
| 45 mins | Thicker | Yolk/135° F. | <10/48 hrs |
| 50 mins | Thicker | Yolk/139° F. | <20/48 hrs |
| 55 mins | Thicker | Yolk/139° F. | <40/48 hrs |
| 60 mins | Thicker | Yolk/139° F. | <10/48 hrs |
| 65 mins | Thicker | Yolk/139° F. | 0/48 hrs |
| 70 mins | Thicker | Yolk/139° F. | <10/48 hrs |
| 75 mins | Thicker, very slight occlusion | Yolk/139° F. | 0/48 hrs |
| 80 mins | Thicker, slight occlusion | Yolk/139° F. | 0/48 hrs |
| 85 mins | Thicker, slight occlusion | Yolk/139° F. | 0/48 hrs |
| 90 mins | Thicker, occlusion | Yolk/139° F. | 0/48 hrs. |

EXAMPLE IV

Medium and large grade eggs stored either at room temperature (70° F.) or at 45° F. for 12 hours were inoculated with Salmonella typhimurium bacteria ($10^6$ gm) either between the shell and outer membranes (outer) or directly into the yolk (inner).

The inoculated eggs were placed in a water bath operated at different times at 134°, 136°, and 138° F. (±0.3° F.). Ten eggs representing each combination of variables (starting temperature, egg size, and pasteurization process temperature) were removed at two-minute intervals beginning after initial heating for 38 minutes and continuing through 50 minutes. This represented 38, 40, 42, 44, 46, 48, or 50 minutes of total heating (TPT). The sampled eggs were cooled to room temperature and analyzed.

For each combination of variables described above (egg size, egg storage temperature, heating time, and heating temperature), another 10 uninoculated eggs processed at the same temperatures and for the same TPT's were utilized for functionality evaluation. After heating/cooling, these eggs were cracked open; and yolk/white color, egg white whipability, and yolk emulsification capacity were evaluated. Eggs of the same size and at the same storage temperature served as controls.

The *Salmonella* kill results appear in Table 4 below.

TABLE 4

| | Salmonella Reduction (percent) | | | | | | | |
|---|---|---|---|---|---|---|---|---|
| | Egg size: | | | | | | | |
| | Medium | | | | Large | | | |
| | Initial egg temp, °F.: | | | | | | | |
| | 70° F. | | 45° F. | | 70° F. | | 45° F. | |
| | Inoculation: | | | | | | | |
| | outer | inner | outer | inner | outer | inner | outer | inner |
| Pasteurization temp, 134° F. | — | — | — | — | — | — | — | — |
| Heating time, min: 38 | 38 | 43 | 35 | 29 | 18 | 40 | 33 | 25 | 15 |
| 40 | 40 | 46 | 38 | 31 | 20 | 45 | 35 | 29 | 18 |
| 42 | 42 | 52 | 43 | 34 | 21 | 50 | 40 | 31 | 20 |
| 44 | 44 | 55 | 45 | 36 | 24 | 53 | 43 | 35 | 22 |
| 46 | 46 | 64 | 52 | 39 | 27 | 60 | 50 | 37 | 25 |
| 48 | 48 | 73 | 64 | 40 | 30 | 70 | 60 | 39 | 27 |
| 50 | 50 | 87 | 72 | 43 | 31 | 85 | 70 | 41 | 30 |
| Pasteurization temp, 136° F. | — | — | — | — | — | — | — | — |
| Heating time, min: 38 | 38 | 47 | 37 | 33 | 23 | 45 | 35 | 30 | 20 |
| 40 | 40 | 50 | 40 | 35 | 25 | 47 | 37 | 33 | 23 |
| 42 | 42 | 55 | 46 | 41 | 29 | 51 | 40 | 40 | 26 |
| 44 | 44 | 58 | 49 | 46 | 31 | 55 | 45 | 44 | 29 |
| 46 | 46 | 67 | 58 | 50 | 34 | 63 | 53 | 48 | 30 |
| 48 | 48 | 81 | 72 | 54 | 36 | 77 | 68 | 50 | 35 |
| 50 | 50 | 93 | 80 | 56 | 38 | 90 | 77 | 53 | 37 |
| Pasteurization temp, 138° F. | — | — | — | — | — | — | — | — |
| Heating time, min: 38 | 38 | 67 | 48 | 65 | 61 | 65 | 45 | 63 | 42 |
| 40 | 40 | 73 | 52 | 70 | 68 | 70 | 50 | 68 | 48 |
| 42 | 42 | 91 | 81 | 87 | 85 | 89 | 80 | 85 | 77 |
| 44 | 44 | 100 | 96 | 96 | 93 | 100 | 94 | 96 | 90 |
| 46 | 46 | 100 | 100 | 100 | 100 | 100 | 100 | 100 | 100 |
| 48 | 48 | 100 | 100 | 100 | 100 | 100 | 100 | 100 | 100 |
| 50 | 50 | 100 | 100 | 100 | 100 | 100 | 100 | 100 | 100 |

Even in the worst case situation (large egg, 45° F. initial temperature, yolk inoculation), a 100 percent bacterial kill was obtained with 46 minutes TPT at 138° F.; and a satisfactory kill was obtained in all tests in which the eggs were processed to levels equivalent to or exceeding the minimum USDA standards for liquid whole eggs.

No egg white separation or coagulation were noted in any of the eggs evaluated in this study. Even the longest heating time (50 min) produced no adverse results. In addition, no changes in egg white and yolk color were observed. Likewise, egg white whipability and egg yolk emulsion stability were not significantly different than in the non-heat processed controls.

EXAMPLE V

For each test, 12 shell eggs at an initial center of yolk temperature of 50°±1.5° F. and varying in size from 54 to 67 gms were placed in the Blue M MAGNAWHIRL precision water bath. The eggs were monitored by a TYPE K, hypodermic probe thermocouple coupled to a Tegam K, J&T, single input TC thermometer. The results were as follows:

TABLE 5

| Pasteurization Temperature | 130° F. | 134° F. | 136° F. | 138° F. |
|---|---|---|---|---|
| Number of Eggs Tested | 260 | 200 | 180 | 180 |
| Average size (gms) | 53 | 60 | 64 | 57 |

TABLE 5-continued

| Average Time Before EqT (min) | 62 | 44 | 40 | 38.5 |
|---|---|---|---|---|
| Range of Time (min) | ±1 | ±1.5 | ±1.5 | ±1.5 |

The size and temperature of an egg entering a pasteurization medium are significant determinants of EqT and TPT. As a rule, for highest food safety, the lower the temperature at which an egg is held (down to about 38° F.), the better. At temperatures below about 45° F., the growth activity of shell egg infections is very low if not static. Any significant holding time before pasteurization at above 55° F. is undesirable since, from that point, the active growth of infectious organisms can be substantial. Virtually all shell eggs which are to be pasteurized should be at a temperature below 50° F. Less than 45° F. is preferred.

EXAMPLE VI

Breakage due to initial process temperature shock can be a significant factor. Usually, the lower the starting egg temperature, the more frequent breakage is. Breaking can be reduced by tempering shell eggs before they are heated to the pasteurization temperature. Tempering is accomplished by employing at least one intermediate, rapid incremental heat exposure step and is described in detail below.

Sixty-four (64) refrigerated fresh eggs (48 hrs old) were inoculated with $10^9$ microorganisms per gram of *Salmonella*

*typhimurium* in distilled water by shell puncture with a Micropoint 0.3 cc syringe. Sixteen (16) medium and 16 large eggs were punctured and injected with 0.2 cc of the culture immediately beneath the shell and outer membranes. Sixteen medium and 16 large eggs were similarly inoculated by puncture through the vitelline membrane to the proximal center of the yolk as visually gauged while viewing the egg through the candling aperture. Each puncture hole was filled with a dab of hot resin, which was allowed to cool for 5 minutes. The eggs were then divided into two groups of 32, each comprised of 16 54±1 gram and 16 68±1 gram eggs with eight eggs of each size being shell inoculated and the other eight being yolk inoculated.

The eggs were placed in separate, precision temperature controlled, water baths, one set at 45° F. and the other at 65° F. After an elapsed time of 60 minutes four 54 gram and four 68 gram eggs from each water bath were punctured by a type K hypodermic thermal probe, and the temperature at the center of the yolk was taken. As measured at the yolk center, all eggs were at a temperature within 1° F. of the bath temperature; i.e., four eggs were at approximately 45° F. and 4 at approximately 70° F. Samples taken from puncture points at the inner shell and yolk center were cultured. The results were: average *Salmonella* for all eggs equalled $10^8$ gm, the range being from $10^5$ to $10^9$ microorganisms per gram.

Inoculated eggs making up the two groups were respectively placed in water baths operating at 136°±0.5° F. and at 138°±0.5° F. After 35 minutes of residence time in the bath, a sample of four eggs was removed and cooled in a water bath set at 40° F. for 15 minutes. Each sample was composed of 54 gm eggs with initial temperatures of 45° and 65° F. and 68 gm eggs with the same initial temperatures.

This sampling procedure was repeated at 2 minute intervals; i.e., after 37, 39, 41, 43, 45, 47 and 49 minutes of TPT. All eggs were analyzed for *Salmonella*.

The remaining 8 eggs were withdrawn and cooled in a water bath at 40° F. These were tested against 8 untreated eggs of comparable age and size for visual appearance, whipability, yolk emulsification, and baking (standard sponge cake) equivalency test.

The results of these tests are presented in the following tables.

TABLE 6

Initial temperature = 45° F.
Process Temperature = 136 ± 0.5° F.

| Egg Size | TPT | Reduction of Salmonella Population (Percent) | |
|---|---|---|---|
| (gm) | (min) | White | Yolk |
| 54 | 35 | 28 | 17 |
| 54 | 37 | 32 | 20 |
| 54 | 39 | 34 | 26 |
| 54 | 41 | 60 | 30 |
| 54 | 43 | 75 | 65 |
| 54 | 45 | 83 | 72 |
| 54 | 47 | 90 | 82 |
| 54 | 49 | 92 | 84 |
| 68 | 35 | 29 | 12 |
| 68 | 37 | 33 | 22 |
| 68 | 39 | 41 | 24 |

TABLE 6-continued

Initial temperature = 45° F.
Process Temperature = 136 ± 0.5° F.

| Egg Size | TPT | Reduction of Salmonella Population (Percent) | |
|---|---|---|---|
| (gm) | (min) | White | Yolk |
| 68 | 41 | 59 | 28 |
| 68 | 43 | 63 | 46 |
| 68 | 45 | 79 | 69 |
| 68 | 47 | 85 | 71 |
| 68 | 49 | 90 | 82 |

TABLE 7

Initial Temperature = 65° F.
Process Temperature = 136 ± 0.5° F.

| Egg Size | TPT | Reduction of Salmonella Population (Percent) | |
|---|---|---|---|
| (gm) | (min) | White | Yolk |
| 54 | 35 | 28 | 17 |
| 54 | 37 | 34 | 23 |
| 54 | 39 | 35 | 25 |
| 54 | 41 | 40 | 29 |
| 54 | 43 | 73 | 61 |
| 54 | 45 | 81 | 76 |
| 54 | 47 | 95 | 85 |
| 54 | 49 | 100 | 92 |
| 68 | 35 | 27 | 12 |
| 68 | 37 | 31 | 19 |
| 68 | 39 | 33 | 24 |
| 68 | 41 | 59 | 28 |
| 68 | 43 | 71 | 51 |
| 68 | 45 | 79 | 71 |
| 68 | 47 | 93 | 80 |
| 68 | 49 | 98 | 88 |

TABLE 8

Initial Temperature = 45° F.
Process Temperature = 138 ± 0.5° F.

| Egg Size | TPT | Reduction of Salmonella Population (Percent) | |
|---|---|---|---|
| (gm) | (min) | White | Yolk |
| 54 | 35 | 38 | 22 |
| 54 | 37 | 45 | 26 |
| 54 | 39 | 51 | 44 |
| 54 | 41 | 71 | 67 |
| 54 | 43 | 96 | 89 |
| 54 | 45 | 100 | 95 |
| 54 | 47 | 100 | 100 |
| 54 | 49 | 100 | 100 |
| 68 | 35 | 31 | 17 |
| 68 | 37 | 41 | 23 |
| 68 | 39 | 48 | 38 |
| 68 | 41 | 57 | 50 |
| 68 | 43 | 89 | 88 |
| 68 | 45 | 99 | 97 |
| 68 | 47 | 100 | 100 |
| 68 | 49 | 100 | 100 |

TABLE 9

Initial Temperature = 65° F.
Process Temperature = 138 ± 0.5° F.

| Egg Size | TPT | Reduction of Salmonella Population (Percent) | |
|---|---|---|---|
| (gm) | (min) | White | Yolk |
| 54 | 35 | 54 | 25 |
| 54 | 37 | 63 | 31 |
| 54 | 39 | 88 | 41 |
| 54 | 41 | 97 | 54 |
| 54 | 43 | 100 | 90 |
| 54 | 45 | 100 | 100 |
| 54 | 47 | 100 | 100 |
| 54 | 49 | 100 | 100 |
| 68 | 35 | 31 | 29 |
| 68 | 37 | 47 | 35 |
| 68 | 39 | 56 | 48 |
| 68 | 41 | 80 | 74 |
| 68 | 43 | 94 | 91 |
| 68 | 45 | 100 | 100 |
| 68 | 47 | 100 | 100 |
| 68 | 49 | 100 | 100 |

Even in the worst case situation, (large egg, 45° F. initial temperature, yolk inoculation), a 100 percent kill was obtained with a TPT of 45 minutes at a pasteurization temperature of 138° F., and a satisfactory kill was obtained after a TPT of about 41 minutes.

Very minor cooking was noted in the whites of about 5 to 10 percent of the smaller eggs with an initial 65° F. temperature processed for 49 minutes at a temperature of 138°±0.5° F. No cooking was observed in any of the other eggs tested. No changes in egg white or yolk color were observed. Egg white whipability and egg yolk emulsion stability were not significantly different than in the unprocessed controls. Sponge cakes baked in accord with National Egg Board recommendations from treated eggs in all four egg size/initial temperature categories were equivalent to those baked from the controls.

The overall appearance of freshness was equivalent to that of freshly laid eggs. There was a noticeable enlargement of the yolks of the eggs in the 65° F. starting temperature group processed for more than 45 minutes but only when the processed eggs were closely compared to the controls. Yolks of eggs processed for TPT's exceeding 45 minutes seemed to rupture more readily than those of the controls when the eggs were cracked onto a hard surface. Additional tests in which treated eggs were chilled for longer periods of time (over 24 hrs at 42° F.) showed that this extended chilling restored the rupture resistance of the processed egg yolks to a breakage level about equal to that of normal yolks.

All treated eggs exhibited Haugh values (thickness of white; industry standard for measuring the freshness of a shell egg) equivalent and in some cases markedly superior to those of controls. Almost 50 percent of the eggs processed for 47 minutes (those weighing 54 and 68 gms whether processed from an initial temperature of 45° F. or 65° F.) exhibited some opacity in the whites. The observed type of opacity is visually indistinguishable from that of eggs which are very fresh or which have become partially occluded prior to significant coagulation or loss of SLP (soluble liquid protein). SLP is a measure of coagulation (see the above-cited Swartzel et al. U.S. Pat. No. 4,957,759).

Vibration of the eggs being processed by shaking or with ultrasonic energy or cavitation is another optional technique that can often be employed to advantage in the processing of eggs according to the principles of the present invention. Vibration promotes the transfer of heat to the inner parts of the egg, making the pasteurization process more efficient and ensuring an optional kill of any infections that may be present, irrespective of that part of the egg in which the infection may be located.

The advantages of employing vibration were demonstrated in the tests described in the following examples.

EXAMPLE VII

Control: 120 medium sized, 52 gm shell eggs at 70° F. were pasteurized at 138° F. in the Blue M water bath. Temperatures were taken at yolk center with the type K hypodermic thermal probe at intervals during a TPT of 37 minutes.

A Treated: same as control except that the eggs were placed on a reciprocating shaker platform located at the bottom of the 138° F. water bath. The platform was reciprocated at a ½ in pitch and at a frequency of 60 to 75 cycles per minute.

B Treated: 120 medium size eggs at an initial temperature of 70° F. were processed in batches of 12 per test (10 tests) in a Branson Type D, Ultrasonic Precision Water Bath set at power level 4 with the water at a temperature of 138° F.

The yolk center temperatures of the eggs at the indicated sampling intervals are presented in the following table.

TABLE 10

| | Average Temperature (°F.) Control | Average Temperature (°F.) Test A | Average Temperature (°F.) Test B |
|---|---|---|---|
| 5 minutes | 100.0 | 101.0 | 101.0 |
| 10 minutes | 122.4 | 124.5 | 123.7 |
| 15 minutes | 125.0 | 126.6 | 127.0 |
| 20 minutes | 128.6 | 130.5 | 131.3 |
| 25 minutes | 133.0 | 135.0 | 135.0 |
| 27 minutes | 134.0 | 135.5 | 136.3 |
| 29 minutes | 135.0 | 136.6 | 137.0 |
| 31 minutes | 135.5 | 137.2 | 137.5 |
| 33 minutes | 135.7 | 137.9 | 137.7 |
| 35 minutes | 136.2 | 138.0 | 138.0 |
| 37 minutes | 137.0 | — | — |

The tabulated results clearly show that the rate of heating of a shell egg can be significantly increased by subjecting the egg to vibration. This translates into a quicker reaching of EqT, with a consequent shortening of TPT and a concomitant reduction in processing costs.

Comparing the EqT of eggs subjected to ultrasonic vibration with controls processed identically (except for ultrasonic vibration) at 136° F. for 44 minutes showed that an average five-to-eight percent increase in heat transfer efficiency was obtained at medium power settings of the Branson Ultrasonic Cleaner. The range of improvement in heat transfer efficiency ranged from three percent to as high as 15 percent.

Tests of eggs from the same batch and inoculated with *Salmonella typhimurium* at a concentration of $10^8$ microorganisms per gram showed an increased reduction of the infection compared to eggs pasteurized under the same conditions for the same time; i.e., 138° F. for 41 minutes, both when ultrasonic energy generated at the same settings and mechanical vibration were employed. The average was an approximately 14 percent greater reduction in the TPT required for destruction of the infection at a given pasteurization process temperature (which can also be translated into a lower temperature for a given TPT). The increase in infection reduction ranged from about 5 percent to 20 percent for the same TPT's at the same process temperatures.

EXAMPLE VIII

One significant discovery arising from the time-at-temperature pasteurization of shell eggs with mechanical vibration is that shell eggs can be scrambled inside the shell by application of the vibratory technique. Tests employed an adjustable, reciprocating flask shaker; an adjustable, orbital test tube mixing pad; and the Branson ultrasonic apparatus. The ultrasonic energy did not produce in-shell-scrambled eggs; the outer membranes of those eggs remained intact. In all tests utilizing mechanical vibration, it was found that shell eggs can be scrambled in the shell over a wide range of frequencies, amplitudes, and process times. Heating the eggs markedly reduced the time need for mechanical vibration to scramble the eggs in-shell.

The foregoing findings were confirmed by tests in which three dozen shell eggs were pasteurized at 139° F. for 50 minutes in a water bath in the Blue M apparatus.

Figure 11:
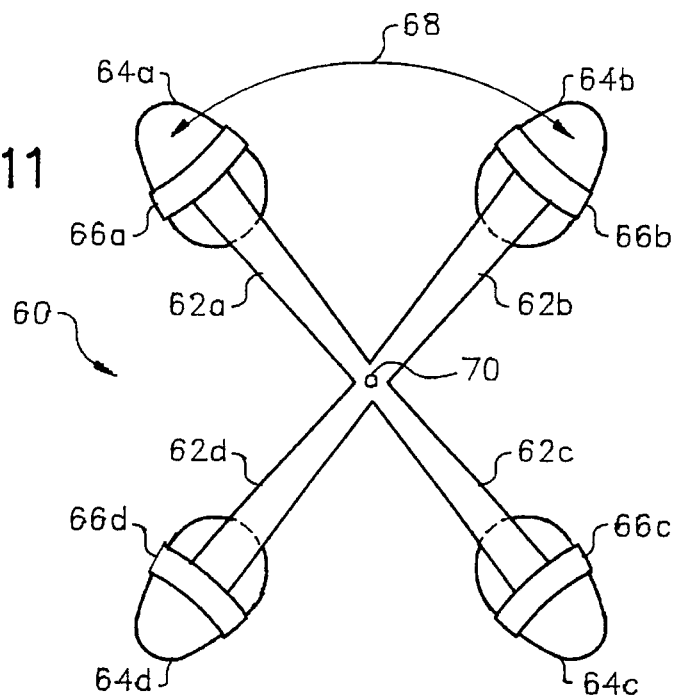
FIG. 11 is a diagrammatic view of one representative device that can be employed to mechanically vibrate whole shell eggs pasteurization processed in accord with the principles of the present invention in order to increase the rate of transfer of heat to the centers of the eggs and, in some cases, to scramble the eggs in their shells.

After removal from the bath and while still very warm to the touch, the eggs were loaded into an orbital shaker and affixed by elastic retainers to the shaker arms as shown diagrammatically in FIG. 11. The shaker is identified by reference character 60, the four arms by reference characters 62a–d, the eggs by reference characters 64a–d, and the elastic retainers by reference characters 66a–d. The shaker arms oscillated over an adjustable throw or amplitude identified by arc 68 about an axis 70. The amplitude was varied over a range of 1/32 in to 5/8 in and the frequency over a range of 50 and 500 cps.

Upon opening, about 60 percent of the eggs which had been vibrated for 7 to 10 minutes at amplitudes between about 1/4 in and 7/16 in were prescrambled in the shell. The prescrambled eggs could be broken directly into a pan and perfectly scrambled.

Heating eggs subjected to vibration facilitated the transfer of heat to internal egg particles by producing contact of the heated shell with all particles inside the egg. This translates into improved pasteurization efficiencies.

Cold eggs were also scrambled, using the orbital shaker and the operating conditions described above. There was less uniformity of scrambling, and there appeared to be some shell membrane tearing. Warming the eggs to a temperature above 130° F. (54.44° C.) alleviated those problems.

Eggs processed with ultrasound were not scrambled.

EXAMPLE IX

Several eggs were tested at much higher frequencies and shorter amplitudes, i.e., between about 700 and 800 cps at a 1/64 in to 1/32 in throw for a total time of about 15 minutes. A very unusual phenomenon occurred. Upon opening the shell, it was found that the egg had become almost entirely one large yolk, there being little or no distinct egg white inside the shell. After a few minutes on a flat surface, however, egg white began to slowly reappear from the yolk. Apparently, the white was worked through pores in the vitelline membrane by the vibrations. The membrane expanded without breaking to compensate for the much greater encompassed volume attributable to the migrated egg white.

EXAMPLE X

It was pointed out above that it is often advantageous in the practice of the present invention to overshoot the selected pasteurization process temperature in the initial heating of the egg(s) being processed and then allow the temperature to drift down to the selected level. This approach has the advantage of increasing the rate of heat transfer through the egg to the yolk which, in effect, shortens EqT and, consequently, TPT. High temperature overshooting may require the use of a heat transfer medium at a temperature which will result in cooking of the white before the RPT required for the wanted pasteurization throughout the mass of the egg including the yolk center is reached.

Up to a point, the higher the overshoot temperature, the greater the rate of heat transfer through the egg. In effect, this results in a desirably reduced EqT. If the egg is placed in water at 145° F., the outer layers will show visible signs of cooking in about 5 to 10 minutes, depending on the size of the egg and its original temperature. However, if the egg is removed from the heat transfer media after a few minutes and before coagulation, the temperature will drop below critical levels at the surface; and the heat imparted by the initial immersion will dissipate rapidly into the egg. If the egg is then immersed in a pasteurization bath (gas, fluid, or liquid) with a temperature lower than the critical temperature producing virtually instant coagulation (about 140° F.), the time required for RPT at the selected pasteurization temperature may be shortened and the egg pasteurization processed without additional risk of coagulating the yolk. This results in a shorter EqT time and a longer RPT for a given TPT and, as a result, more effective destruction of infective organisms than is otherwise possible.

A typical overshoot temperature ranges from 139°–150° F. The overshoot temperature is used for about 2 to 3 minutes and is followed by a decrease to a process temperature in the 130° to 139+° F. range (but below 140° F.). The time employed will vary with the size or load of the eggs and the starting temperature of the eggs. The lower the pasteurization temperature selected, the higher the overshoot temperature which can be conveniently used. Higher pasteurization temperatures require closer controls and reduced time to prevent visible coagulation.

The advantages of employing overshoot (or intermittent pasteurization were demonstrated by a representative test in which 12 medium sized eggs at a preprocessing temperature of 55° F. were tempered in water at 132° F. for 3 minutes, removed from the water bath, allowed to dwell for 3 minutes in room temperature air, and then introduced into a 138° F. water batch in the Blue M apparatus. The following temperatures were measured: non-yolk portion of the tempered egg next to its shell, 131° F.; the middle portion of the white, 112° F.; the white adjacent the yolk, 77° F.; the outer edge of the yolk, 58° F.; the center of the yolk, 56° F.

Thus tempered eggs were also placed in a water bath at a temperature of 143° F. (above the coagulation point of egg white albumin), and the water bath temperature controller was at that time reset to 138° F.

Results

The time required to reach EqT of the eggs started at 143° F. was shortened by an average of 10 percent with no noticeable diminution in egg quality. This permits processing at preferred pasteurization temperatures while reducing TPT by about 5 to 8 percent.

By the time heat transferred through the shells into the outermost layers of the egg albumin (about 4 to 5 minutes), the temperature of the pasteurization medium dropped to a baseline temperature of 138° F. In this short period of time, not enough heat can transfer through the shell and outer membrane to coagulate the outer layers of albumin. At the same time and as discussed above, the faster rate of heat transfer obtained by employing the higher, initial, overshoot temperature decreases EqT and, consequently, TPT.

Much higher temperatures can be used to reduce EqT; but requirements for closer process parameter controls to prevent increased thermal shock breakage and risks of coagulation will be limiting factors. These limiting factors depend upon the quantity of the product pasteurized and the particular conditions employed for pasteurization.

While the preferred "overshoot" temperature will typically be between 139° F. and 150° F., this temperature can range up to about 170° F. The process parameter tolerances at this point, however, are so close that these higher overshoot temperatures, for all practical purposes, become more or less the same as those required the flash tempering technique described hereinafter.

EXAMPLE XI

Another technique that can be employed to advantage in the practice of the present invention is to pulse the pasteurization process temperature; i.e., cycle that temperature between low and high levels. This is beneficial because pasteurization temperatures high enough to otherwise cause coagulation can be employed if alternated periodically with less critical and lower but effective pasteurization temperatures. This approach enhances heat transfer to the egg center without coagulation of the white. This reduces TPT as a result of a reduced EqT time.

Preferred intermittent/periodic temperatures of the pasteurization medium are between about 130° and 138° F. on the low side and about 139.5° and 145° F. on the high side. These temperatures are within a practical range for pulsing. Eggs being pasteurized can effectively be alternatively treated at a baseline pasteurization temperature of 130° F. or higher and a pulse temperature of 139° F. to 145° F. or even higher, provided that the time of exposure at the higher temperature is limited to a time shorter than that which will cause coagulation of the white at the selected high side or pulse temperature. However, closer control over the process parameters must be exercised when using higher pulse temperatures.

As an alternative to pulsing in the same media, eggs may be transferred between baseline temperature heat transfer media and higher pulse temperature transfer media. Also possible are combinations of techniques which employ one or more high side pulse and baseline temperatures and one or more pasteurization media to effect optimal pasteurization while working below critical coagulation times and temperatures and providing the most efficient EqT.

To demonstrate the efficacy of the just-described pulsing techniques, 60 gram eggs were heated at 145° F. for 2 minutes. The eggs were then held at ambient temperature for a dwell time of 2 minutes. This was followed by heating the eggs at 140° F. for 2 minutes and then heating them at 130° F. for 38 minutes.

EqT was reached after 35 minutes. This was 4 minutes faster than controls heated at 138° F. This represents an 11 percent decrease in EqT.

EXAMPLE XII

The percentage of eggs damaged by cracking increases as the differential between the initial and pasteurization process temperatures increases. That is, the more severe the temperature differential, the more eggs that will crack. This number can become substantial when shell eggs are subjected to the temperatures at the upper end of the useful pasteurization temperature range. To overcome this serious problem, the shell eggs are preferably raised to process temperatures in at least one and preferably two or more steps. This process of heating eggs from their initial temperature to the pasteurization temperature in stages to reduce breakage and for other purposes is referred to herein as tempering.

Tempering is typically accomplished by holding the eggs in air, preferably in a sanitary enclosure at one or more intermediate temperatures in the range of 65° to 131° F. for a total period of 10 minutes to 24 hours with the particular time(s) and temperature(s) depending on such factors as: the temperature conditions under which the eggs were heretofore held; the size of the eggs; the baseline pasteurization temperature to be used; and whether or not basic process aids such as turbulence, vibration, and/or heat transfer promoting pulsing treatments are to be used.

While not preferred, the minimum tempering temperature can be substantially lower than 130° F. Particularly when tempering temperatures below 130° F. are used, the tempering time should be no more than is required to reduce breakage when the egg is subsequently subjected to primary pasteurization because <130° F. temperatures promote the growth of *Salmonella* and other dangerous microorganisms.

Tempering quickly to prevent any significant growth of infections including those superficially present at the inner shell surface or those at the center of the yolk can be accomplished by flash tempering, which consists of first exposing the shell egg for a brief period of time to a higher temperature than could be employed if the eggs were exposed to it for an appreciable length of time.

The temperature for flash tempering can be considerably higher than 212° F.; and such temperatures can be reached by exposing the eggs to steam or an open flame, for example. Unless care is exercised, however, the use of these super high flash tempering temperatures can result in scorched or "off" odors and/or flavors in the egg. Consequently, the time of exposure for the temperature selected should be no more than is absolutely necessary to reduce breakage during processing to avoid imparting any "off" odor or flavor to the egg.

In all cases where tempering is utilized, the dwell or post-tempering time before entry into primary pasteurization should be of the minimum duration required for the tempering heat imparted to the egg to function to reduce subsequent breakage. This breakage reducing function may occur during tempering and also subsequently during the dwell or post-tempering period and during pasteurization. The total of tempering and post-tempering or dwell times is preferably from about 0.5 minutes at the highest temperatures (ca. 212° F. to steam and open flame temperatures) to 40 minutes.

Tempering at more modest temperatures (134.5° to 138.5° F.) is preferably accomplished by heating the eggs being processed in one or more stages with the eggs being treated in the last stage at a maximum temperature of 138.5° F. for about 1 minute with a minimum dwell time afterwards of about 3 minutes. The total time (heating and dwell) is in the range of 1 to 15 minutes. Most generally preferred for a wide variety of processing applications are tempering temperatures in the range of 130° to 131° F. for total times of 5 to 50 minutes with 5 to 10 minutes being preferred.

The following table gives preferred pasteurization process parameters (times at temperatures for eggs flash tempered by heating them at a representative 146° F. for 2 minutes, this being followed by a dwell at room temperature of 5 minutes).

TABLE 11

| Shell Eggs at 73° F. | | |
|---|---|---|
| Weight | Temperature (°F.) | TPT (min) |
| 40–60 | 138.5 ± 0.7 | 35–43 |
| 60–80 | 138.0 ± 0.5 | 36–45 |

Preferred process conditions for eggs representatively tempered at 125° F. for 2–3 minutes with a 3–5 minute dwell appear in Table 12.

TABLE 12

| Shell Eggs at 68° F. | | |
|---|---|---|
| Weight | Temperature (°F.) | TPT (min) |
| 40–60 | 138.5 ± 0.7 | 37–45 |
| 60–80 | 138.0 ± 0.5 | 38–47 |

Tempering as usually accomplished in 5 to 10 minute steps may typically add about 1 to 5 minutes to TPT. Tempering and/or prepackaging and/or coating steps employed to overcome cracking may significantly increase the overall process time, especially in applications employing more severe treatment regimes in the range of from about 135° F. to about 140° F.

If accomplished within the specified parameters, tempering does not necessarily cause any significant increase in TPT or increase in infections but can significantly reduce EqT and cracking of shells and otherwise contribute to the overall effectiveness of the pasteurization process.

Tempering times will in general be inversely proportional to the tempering temperatures that are employed. That is, the higher tempering temperatures will be employed for the shorter indicated periods of time and vice versa. This avoids coagulation, thermal shock induced cracking of egg shells, and other problems which might otherwise occur.

The following representative tests employed tempering in pasteurizing eggs in accord with the principles of the present invention.

Control: 36 medium sized eggs at an initial temperature of 65° F. were divided into four batches of nine each. The batches were processed separately and introduced directly into a water pasteurization bath temperature regulated with a controller preset at 138° F. The eggs were held in the pasteurization bath for 20 minutes TPT.

The eggs were removed from the bath at the end of the 20 minute period and examined for cracks.

Results:
Batch 1: Broken eggs=2
Batch 2: Broken eggs=0
Batch 3: Broken eggs=1
Batch 4: Broken eggs=1

A Tempered eggs: 36 medium sized eggs at an initial temperature of 65° F. were divided into four batches of nine each. The batches were processed separately in a water bath regulated by a temperature controller set at 130° F. for 5 minutes and then transferred to a water pasteurization bath at 138° F. for 15 minutes TPT.

Results:
Batch 1: Broken eggs=0
Batch 2: Broken eggs=1
Batch 3: Broken eggs=0
Batch 4: Broken eggs=0

B Tempered Eggs: 36 medium sized eggs at an initial temperature of 65° F. were divided into batches of nine eggs, and the four batches were processed separately in an air box 12 in×10 in×24 in. Air preheated to 80° F. was circulated through the box at a rate of 15 cfm for 15 minutes to temper the eggs. Each batch of eggs was then removed from the box and transferred to the 138° F. water pasteurization bath for 15 minutes TPT.

Results:
Batch 1: Broken eggs=0
Batch 2: Broken eggs=0
Batch 3: Broken eggs=0
Batch 4: Broken eggs=0

The reduction in thermal shock cracking afforded by tempering as well as an increased thermal tolerance can be obtained by wrapping, bagging, coating, or otherwise encapsulating the eggs being treated before they are introduced into the pasteurization medium.

The application of these techniques to time-at-temperature egg pasteurization as disclosed herein is illustrated in the following examples.

EXAMPLE XIII

Thirty-six (36) medium sized eggs at an initial temperature of 65° F. were individually tightly wrapped in a Saran® wrap film commonly used for wrapping meat and divided into four batches. The four batches of wrapped eggs were pasteurization processed separately in the 138° F. water pasteurization bath for 20 minutes TPT.

Results:
Batch 1: Broken eggs=0
Batch 2: Broken eggs=0
Batch 3: Broken eggs=0
Batch 4: Broken eggs=1

EXAMPLE XIV

Thirty-six (36) medium sized eggs at an initial temperature of 65° F. were divided into four batches of nine and individually sealed in resealable 5 in×6 in Zip Loc® sandwich bags. The four batches of bagged eggs were separately processed in the 138° F. water pasteurization bath for 20 minutes TPT.

Results:
Batch 1: Broken eggs=0
Batch 2: Broken eggs=1
Batch 3: Broken eggs=0
Batch 4: Broken eggs=0

EXAMPLE XV

Thirty-six (36) medium sized eggs at an initial temperature of 65° F. were divided into four nine-egg batches and individually sealed by spraying the shells with a clear acrylic spray (Krylon® 12 ounce spray-on acrylic coating) The coatings were air dried at 70° F., and the coated eggs were then immersed in the 138° F. water pasteurization bath for 20 minutes TPT.

Results:

Batch 1: Broken eggs=0

Batch 2: Broken eggs=1

Batch 3: Broken eggs=0

Batch 4: Broken eggs=1

Of considerable importance in the practice of the present invention is the handling and packaging or treatment of the processed egg(s) in a manner which will keep the eggs from being recontaminated with harmful organisms. Recontamination can be avoided by packaging the eggs immediately before pasteurization or immediately after pasteurization and before cooling or exposure to eliminate potential contamination by handling or contact with the ambient environment or non-sterile surfaces.

A preferred technique which can be employed involves: (a) individually prepackaging the eggs in a polymeric film formed separately around each egg, (b) sealing the packages, and then (c) pasteurizing the eggs in accord with the principles of the present invention.

This approach has the advantages of: reductions in handling and the above-described thermal shock breakage, elimination of recontamination, and easier control over the process since eggs may be pasteurized continuously on a packed belt line and the individual egg packages then cut apart or otherwise separated. Once sealed in film, the egg does not need to be pasteurized or handled in an aseptic environment. Also, this keeps processing aids such as shell treatment agents from coming off during processing.

Alternative techniques that can be utilized include sealed packaging in Cry-O-Vac® polymers and processing before or after sealing (preferably before).

Spoilage preventing inert gases such as carbon dioxide and nitrogen may be substituted for the air in the packages or added to the eggs by infusion or the use of negative and/or positive pressures as described in above-cited parent application Ser. No. 746,940. The packaging may be sterilized before use to eliminate any harmful microorganisms present on the packaging.

The following examples describe in detail representative applications of a packaging technique as just described in the pasteurization of eggs by the principles elucidated herein.

EXAMPLE XVI

Eight (8) 60 gm eggs tempered at 140° F. for 5 minutes in circulating air were removed from the tempering unit and immediately placed in a 500 ml beaker filled with $CO_2$ at 32° F. for 2 minutes. The eggs were removed from the beaker and placed in 4 in×4 in Seal-A-Meal® bags, which were immediately sealed. The eggs were in-bag pasteurized at 138° F. in a water bath and examined after 40 minutes at 5 minute intervals. The eggs showed no significant occlusion after pasteurization for 75 minutes.

Controls were all occluded after 68 minutes. This indicates that the $CO_2$ taken up in the eggs produced an at least 10% increase in heat tolerance. This is important in circumstances requiring that the egg be heated at a maximum or near maximum permissible temperature for the maximum length of time—for example, if heavy or widespread contamination throughout the mass of the egg with an infection is suspected.

The test was repeated at an otherwise unacceptably high 140° F. pasteurization temperature with the eggs being cracked every 2 minutes after 6 minutes pasteurization elapsed. $CO_2$ treated eggs showed little or no occlusion until after 18–20 minutes of pasteurization. Controls showed signs of occlusion after 12–14 minutes.

EXAMPLE XVII

Thirty-six (36) eggs inoculated through the shell with *Salmonella typhimurium* ($10^9$ gm) were divided into four nine-egg batches and placed individually in 4 in×4 in Seal-A-Meal® bags to which 6 gms each of dry ice (frozen $CO_2$) had just been added. The bags were sealed; and each batch of bagged eggs was separately processed in the 138° F. water pasteurization bath for 40 minutes TPT. Four eggs were then removed from the pasteurization bath in each run and analyzed.

| Results: | |
| --- | --- |
| | Average Reduction in Bacteria (percent) |
| Batch 1: | ~70 |
| Batch 2: | ~80 |
| Batch 3: | ~60 |
| Batch 4: | ~70 |

The remaining eggs in each bath were processed an additional 2 minutes, removed from the bath, and analyzed.

| Results: | |
| --- | --- |
| | Average Reduction in Bacteria (percent) |
| Batch 1: | ~100 |
| Batch 2: | ~80 |
| Batch 3: | ~90 |
| Batch 4: | ~90 |

As a consequence of adding $CO_2$ to the bags, it was possible to pasteurize the eggs for longer periods or at slightly higher temperatures with delayed occlusion (cooking). Both approaches permit better kills of infections.

EXAMPLE XVIII

Mild, safely consumable acids can also be used to increase the resistance of eggs to occlusion or coagulation of the whites, to reduce the loss of functionality, and to reduce other forms of degradation during time at temperature pasteurization.

This aspect of the invention is illustrated by the following tests:

Control

Thirty-six (36) medium sized eggs were each inoculated through the shell with 0.05 mls distilled water carrying a *Salmonella typhimurium* culture at a rate of $10^9$ gm and divided into four batches of nine eggs each. The four batches were separately processed in a 138° F. water pasteurization bath for 40 minutes. Four eggs of each batch were removed from the bath and analyzed.

Results:

| | Average Reduction in Bacteria (percent) |
|---|---|
| Batch 1: | ~60 |
| Batch 2: | ~60 |
| Batch 3: | ~60 |
| Batch 4: | ~70 |

The remaining eggs were processed an additional 2 minutes, and the bacteria kill was measured in the manner just described:

Results:

| | Average Reduction in Bacteria (percent) |
|---|---|
| Batch 1: | ~70 |
| Batch 2: | ~70 |
| Batch 3: | ~80 |
| Batch 4: | ~70 |

Acid processed: The eggs in four nine-egg batches were inoculated through the shell with *Salmonella typhimurium* ($10^9$ microorganisms per gram) in the same manner as the controls. The four batches of inoculated eggs were separately pasteurization processed in the 138° F. water bath to which 0.2% volume percent of citric acid had been added for 40 minutes. Four eggs were removed from each batch, and the bacteria kill was measured.

Results:

| | Average Reduction in Bacteria (percent) |
|---|---|
| Batch 1: | ~60 |
| Batch 2: | ~80 |
| Batch 3: | ~70 |
| Batch 4: | ~70 |

The remaining eggs of each batch were processed an additional 2 minutes and the bacteria kill measured.

Results:

| | Average Reduction in Bacteria (percent) |
|---|---|
| Batch 1: | ~90 |
| Batch 2: | ~80 |
| Batch 3: | ~90 |
| Batch 4: | ~70 |

The increased level of bacterial kill is significant, especially in the case of the eggs pasteurized for the additional 2 minutes.

Citric acid may be used for the purposes just described in concentrations ranging from 0.05 to 0.5 percent based on the volume of the bath. Other acids which can be employed for the purposes just described include the above-mentioned ascorbic, benzoic, and lactic.

As discussed in detail in the working examples and elsewhere above, processes employing the principles of the present invention are designed to make shell poultry eggs safer to eat by destroying harmful organisms superficially resident on the outer surface of the shell and throughout the shell and interior of the egg without impairing the functionality of the egg or altering its organoleptic properties by holding the shell eggs under time/temperature conditions which will destroy harmful bacteria on and inside the egg shells.

Figure 12:
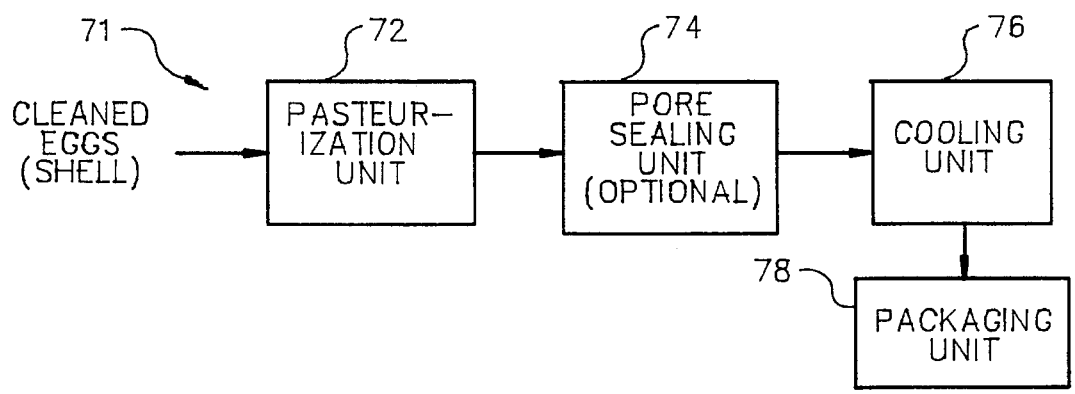
FIG. 12 is a schematic view of a second system for processing whole shell eggs for improved food safety in accord with the principles of the present invention.

One system in which a process of this character can be carried out is illustrated in FIG. 12 and identified by reference character 71. That system includes a holding vessel or pasteurization tank 72, an optionally employed pore sealing unit 74, a heat exchanger 76, and a packaging unit 78.

As is discussed elsewhere in this specification, the initial step in treating whole eggs in a system like that identified by reference character 71 is to clean and, typically, disinfect the outer surfaces of the shell eggs.

The cleaned eggs are transferred to tank 72 where they are held in water or another pasteurization medium at the temperature and for the time selected to reduce any infection located anywhere in the mass of the eggs to a level at least equivalent to that obtained by pasteurizing liquid whole eggs to USDA minimum or protracted standards.

Thereafter, the treated shell eggs can be transferred to heat exchanger 76 to rapidly reduce their temperature to a level which is below that at which growth of any remaining viable bacteria might be a problem and appropriate for packaging. Then, the now cooler eggs are transferred to packaging unit 78 where they are placed in cartons or other containers.

Optionally, the pores and the shells of the treated eggs can be treated with palm stearine or other sealing agent before they are packaged in unit 78. This keeps infectious microorganisms as well as oxygen-containing and other unwanted gases from contaminating the pasteurized egg by penetrating through the pores in the egg shells to the interior of the egg, thereby reducing degradation, preserving food safety, and improving the keeping quality of the treated egg.

Figure 13:
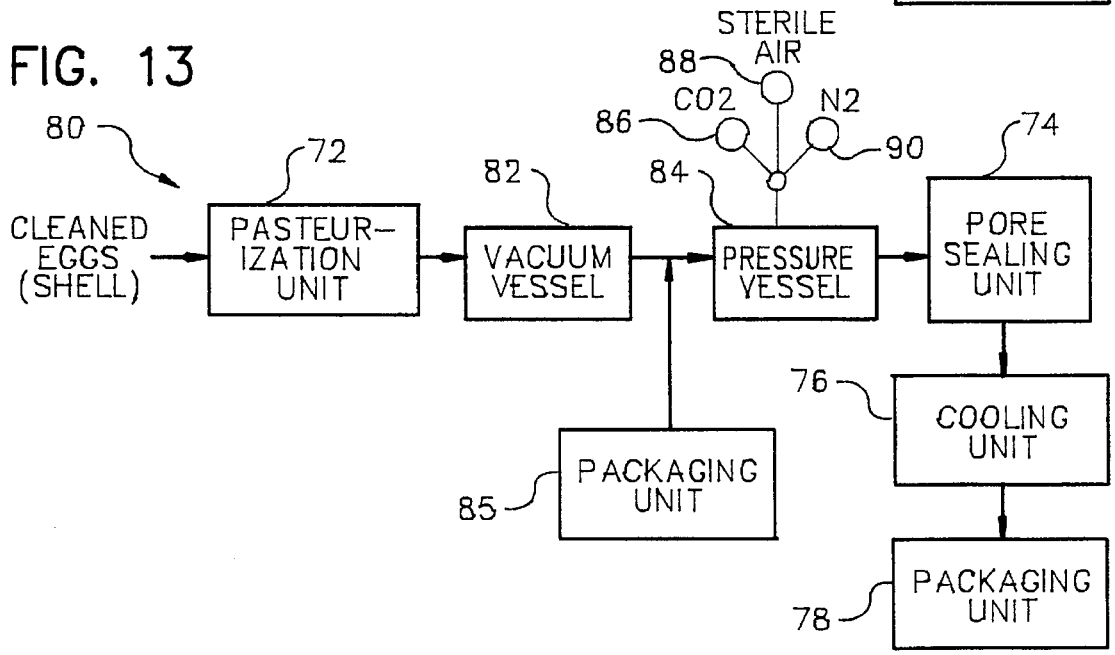

It was also pointed out above that the keeping quality and food safety of eggs treated in the manner just described can often be even further improved by evacuating indigenous gases from the interior of the egg shell and replacing the evacuated gases with inert gases before the pores of the egg shell are sealed. A system for carrying out this process is illustrated in FIG. 13 and identified by reference character 80.

That system includes pasteurization vessel 72; vacuum vessel 82; packaging unit of 85; pressure vessel 84; sources 86, 88, and 90 of carbon dioxide, sterile air, and nitrogen; pore sealing unit 74 (optional); heat exchanger 76; and packaging unit 78.

Cleaned and treated eggs are transferred from the tank 72 in which they are pasteurized to vacuum tank 82. Here, they are held under negative pressure for a period long enough to draw unwanted, indigenous gases from the interior of the egg through the pores in its shell. Of concern are those gases such as oxygen that might cause unwanted chemical reactions; e.g., those that produce spoilage.

From vacuum unit 82, the shell eggs are transferred, still under a negative pressure, to pressure vessel 84. Sterile gas is introduced into the vessel from one or more of the sources 86 . . . 90 under pressure; and the eggs are held in this pressurized environment for a period long enough for the selected gas or mixture of gases to infuse through the pores in the egg shell and fill the interstices in those parts of the egg within the shell.

Thereafter, the treated shell eggs may be cooled in heat exchanger 76 and packaged in unit 78. Alternatively, the pores in the egg shells may first be sealed in unit 74 to prevent unwanted exchanges between gas infused into the eggs through the pores in their shells and gases in the surrounding environs.

Also, in using system 80, the pasteurized eggs may be packaged before they are cooled in order to decrease the chances of recontamination before the eggs are cooled. In this case packaging unit 85 is employed, and unit 74 is deactivated. The package may be filled with an atmosphere-modifying gas of the character and for the purposes discussed above in pressure vessel 84.

Figure 14:
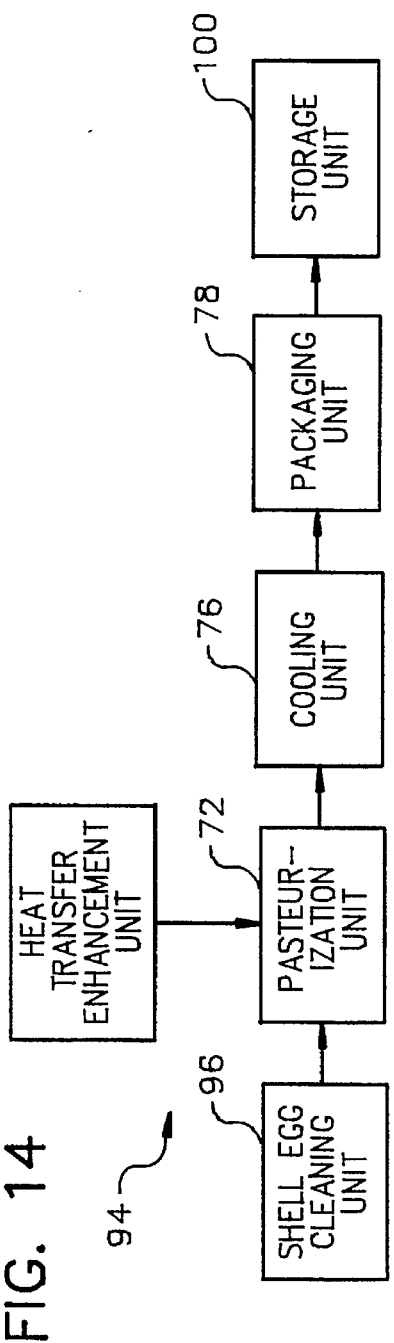

Referring still to the drawing, FIG. 14 discloses another "basic" system 94 for processing whole shell eggs which includes pasteurization unit 72 and cooling unit 78 and, in addition: a shell egg cleaning unit 96, a packaging unit 98, and a storage unit 100 for the packaged eggs. Cleaning unit 96 is conventional and is employed to superficially clean the exteriors of the eggs being processed before they are introduced into pasteurization unit 72.

Packaging unit 98 is also conventional. Here, the eggs are placed in cartons or other packages including those designed to hold only a single egg.

The term storage unit is employed generically. This may be, at various times, and even for the same eggs, a refrigerated warehouse or truck or the cooler at a retail outlet.

Figure 15:
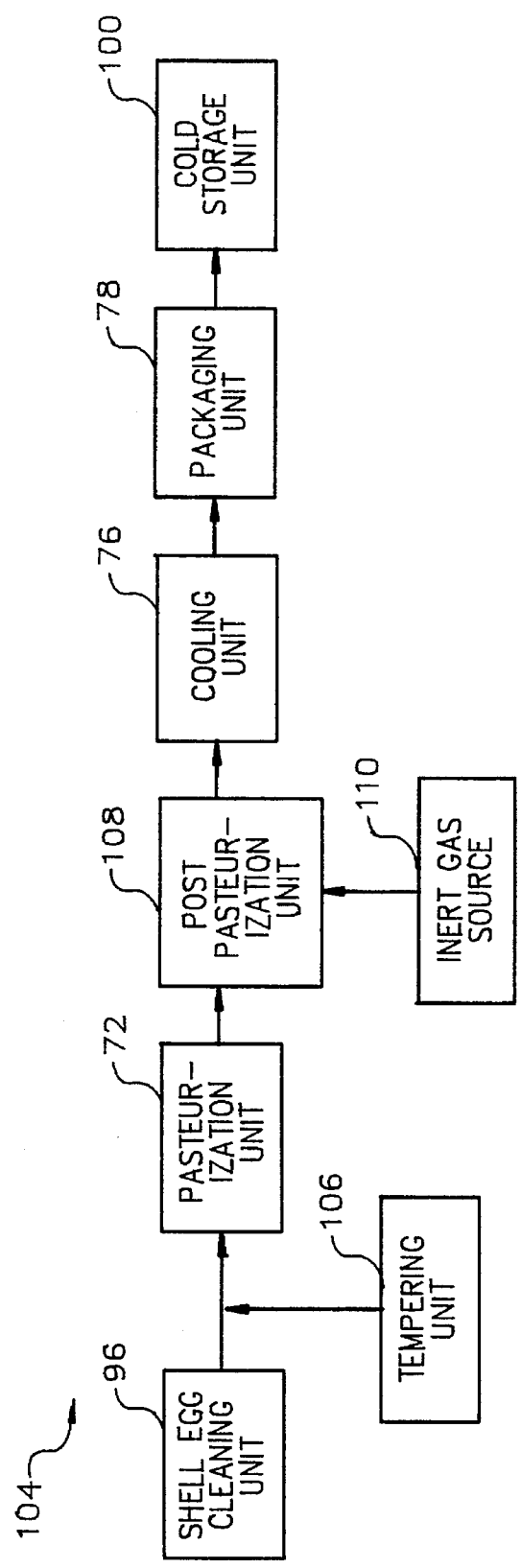

The whole shell egg processing system 104 depicted in FIG. 15 differs from the processing system 94 just described primarily by the addition of a tempering unit 106; a post-pasteurization unit 108; and, optionally, a source 110 of an inert gas such as carbon dioxide, nitrogen, or a mixture of the foregoing.

Tempering unit 106 is used vide EXAMPLE XII above and elsewhere in this specification to reduce breakage of the eggs being processed, a technique which is particularly useful when the differential between the initial egg temperature and the pasteurization process temperature is large and the risk of breakage is accordingly high. Post-pasteurization unit 108 is employed to treat the eggs to prevent recontamination by sealing the pores of the egg shells as discussed above or by packaging the eggs. If the latter technique is adopted, unit 110 may optionally be employed to fill the packages with an atmosphere modifying gas of the character and for the purposes discussed above.

Depicted in FIG. 16 is a shell egg processing system 112 which differs from the FIG. 14 system 94 primarily by the addition of an egg packaging unit 114, an optional inert gas source 116, and a package filling and sealing unit 118.

Packaging unit 114 is employed vide examples XIII–XVII and for the purposes described in those examples and elsewhere in the specification to package the eggs cleaned in unit 96 before they are pasteurized. An inert gas from source 116 may optionally be employed to fill the packages before they are sealed and transferred to pasteurization unit 72. Alternatively, as indicated by reference character 118, the packaged eggs may be optionally filled with a sterile inert gas and sealed immediately after they are pasteurized and before they are transferred to cooling unit 78.

As discussed above, it is possible to significantly shorten the time required to reach EqT in processing eggs for improved safety in accord with the principles of the present invention by: first heating the eggs to a temperature above that at which they can be heated for a time equivalent or exceeding the minimum mandated by the USDA for liquid whole eggs, then holding the eggs for a dwell period in which the heat soaks into the eggs, and then pasteurizing the eggs at the selected temperature in the range specified above. A unit for processing whole shell eggs in the manner just described is depicted in FIG. 17 and identified by reference character 122. That system differs from the basic system illustrated in FIG. 14 primarily by the interposition of an overshoot unit 124 between shell egg cleaning unit 96 and pasteurization unit 72. The medium in which the eggs are heated in overshoot unit 124 may be any of those indicated above to be suitable for use in pasteurization unit 72.

The invention may be embodied in many forms without departing from the spirit or essential characteristics of the invention. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What is claimed is:

1. A method of making a poultry shell egg safer to eat, said method comprising the steps of:

promoting the transfer of heat to the egg by first heating said egg at a temperature above that at which the white of the egg will coagulate but not higher than about 170° F. but for a sufficiently short period of time to preclude significant coagulation of said white; and then heating said egg at a second, lower, pasteurization temperature in the range of 130° F. to <140° F. and below the coagulation temperature of the egg white for a time sufficient to destroy infectious microorganisms throughout the mass of the egg.

2. A method of improving the food safety quality of a poultry shell egg, said method comprising the steps of:

promoting the transfer of heat to the egg by heating the egg at a first, higher temperature above that at which the white of the egg will coagulate and in the range of 139° to about 170° F. but for a sufficiently short period of time to preclude significant coagulation of said white; and then heating said egg at a second, lower pasteurization temperature of at least 130° F. and below the coagulation temperature of the egg white for a time sufficient to destroy infectious microorganisms throughout the mass of the egg.

3. A method as defined in claim 2 in which the egg is first heated at a temperature in the range of 139° to 150° F. for a period of 2 to 3 minutes and is then heated at a pasteurization temperature in the range of 130° to less than 140° F.

* * * * *